US011229673B2

(12) United States Patent
Birchwood

(10) Patent No.: US 11,229,673 B2
(45) Date of Patent: Jan. 25, 2022

(54) METHODS FOR IMPROVING THE QUALITY OF LIFE OF A PATIENT WITH A PEANUT ALLERGY

(71) Applicant: Société des Produits Nestlé S.A., Vevey (CH)

(72) Inventor: Christine Birchwood, East Palo Alto, CA (US)

(73) Assignee: Société des Produits Nestlé S.A., Vevey (CH)

(*) Notice: Subject to any disclaimer, the term of this patent is extended or adjusted under 35 U.S.C. 154(b) by 0 days.

(21) Appl. No.: 16/870,696

(22) Filed: May 8, 2020

(65) Prior Publication Data
US 2020/0368304 A1 Nov. 26, 2020

Related U.S. Application Data

(60) Provisional application No. 62/967,948, filed on Jan. 30, 2020, provisional application No. 62/855,384, filed on May 31, 2019, provisional application No. 62/846,481, filed on May 10, 2019.

(51) Int. Cl.
A61K 36/48 (2006.01)
A61P 37/08 (2006.01)
A61K 9/00 (2006.01)

(52) U.S. Cl.
CPC ............ A61K 36/48 (2013.01); A61K 9/0053 (2013.01); A61P 37/08 (2018.01)

(58) Field of Classification Search
None
See application file for complete search history.

(56) References Cited

U.S. PATENT DOCUMENTS

| 3,809,767 | A | 5/1974 | Sair et al. |
|---|---|---|---|
| 9,198,869 | B2 | 12/2015 | Walser |
| 9,481,716 | B2 * | 11/2016 | Clark ...................... A61P 37/08 |
| 9,492,535 | B2 | 11/2016 | Walser |
| 9,815,894 | B2 | 11/2017 | O'brien et al. |
| 9,949,958 | B2 | 4/2018 | Forbes |
| 9,955,718 | B2 | 5/2018 | Gillespie |
| 9,999,600 | B2 | 6/2018 | Sosin |
| 10,086,068 | B2 | 10/2018 | Walser |
| 10,266,588 | B2 | 4/2019 | Macdonald et al. |
| 10,278,964 | B2 | 5/2019 | Mann et al. |
| 10,286,018 | B2 | 5/2019 | Smith |
| 10,449,118 | B2 | 10/2019 | Walser |
| D866,320 | S | 11/2019 | Bennett et al. |
| D866,321 | S | 11/2019 | Bennett et al. |
| D866,322 | S | 11/2019 | Bennett et al. |
| 10,512,686 | B2 | 12/2019 | Walser |
| 10,653,773 | B2 | 5/2020 | Walser |
| 10,918,676 | B2 | 2/2021 | Raff |
| 2002/0018778 | A1 | 2/2002 | Caplan |
| 2004/0166123 | A1 | 8/2004 | Jacobi |
| 2004/0234548 | A1 | 11/2004 | Caplan |
| 2008/0317878 | A1 | 12/2008 | Li et al. |
| 2009/0111702 | A1 | 4/2009 | Sampson et al. |
| 2011/0243994 | A1 | 10/2011 | Asari et al. |
| 2012/0164306 | A1 | 6/2012 | Girsh |
| 2013/0090344 | A1 | 4/2013 | Thakur et al. |
| 2014/0093541 | A1 | 4/2014 | Clark |
| 2014/0207105 | A1 | 7/2014 | Laulicht et al. |
| 2014/0271721 | A1 | 9/2014 | Walser |
| 2014/0271836 | A1 | 9/2014 | Walser |
| 2014/0363470 | A1 | 12/2014 | Koppelman et al. |
| 2015/0343075 | A1 | 12/2015 | Raff |
| 2016/0030289 | A1 | 2/2016 | Walser |
| 2016/0051593 | A1 | 2/2016 | Raff |
| 2016/0051639 | A1 | 2/2016 | Raff |
| 2017/0021012 | A1 | 1/2017 | Walser |
| 2018/0042816 | A1 | 2/2018 | Walser |
| 2018/0200361 | A1 | 7/2018 | Simon |
| 2019/0167785 | A1 * | 6/2019 | Dilly .................. G01N 33/6854 |
| 2019/0175723 | A1 | 6/2019 | Walser |
| 2019/0192652 | A1 | 6/2019 | Walser |
| 2019/0247444 | A1 | 8/2019 | Raff |
| 2020/0030187 | A1 | 1/2020 | Bennett |
| 2020/0054738 | A1 * | 2/2020 | Adelman ............. A61K 9/0053 |

(Continued)

FOREIGN PATENT DOCUMENTS

| JP | 2003128697 A | 5/2003 |
|---|---|---|
| JP | 2006519187 A | 8/2006 |

(Continued)

OTHER PUBLICATIONS

Van Der Velde J. et al. Development, Validity and Reliability of the Food Allergy Independent Measure (FAIM). Allergy 65(5)630-635, Apr. 2010. (Year: 2010).*
Chan, C. et al. Current Trend in Immunotherapy for Peanut Allergy. Int Reviews of Immunology 37(6)279-290, 2018. (Year: 2018).*
Epstein-Rigbi, N. et al. Quality of Life of Food Allergic Patients Before, During, and After Oral Immunotherapy. J of Allergy and Clinical Immunology: In Practice 7(2)429-436 Feb. 2019. (Year: 2019).*
Anagnostou, K. et al. Assessing the Efficacy of Oral Immunotherapy for the Desensitisation of Peanut Allergy in Children. Lancet 383:1297-304, 2014. (Year: 2014).*
Chu, D. et al. Oral Immunotherapy for Peanut Allergy. Lancet 393:2222-2232, Apr. 25, 2019. (Year: 2019).*

(Continued)

Primary Examiner — Ralph J Gitomer
(74) Attorney, Agent, or Firm — Morrison & Foerster LLP

(57) ABSTRACT

The present disclosure relates to methods of improving the quality of life of a subject having a peanut allergy. In certain embodiments, the disclosure provides methods for improving the quality of life of a subject having a peanut allergy by administering a peanut composition according to an oral immunotherapy schedule. In certain embodiments, the disclosure provides methods for improving the quality of life of a subject having a peanut allergy by informing the subject they are to be, or are being, administered a peanut composition according to an oral immunotherapy schedule.

33 Claims, 6 Drawing Sheets

(56) References Cited

U.S. PATENT DOCUMENTS

| | | |
|---|---|---|
| 2020/0129378 A1 | 4/2020 | Walser |
| 2020/0230206 A1 | 7/2020 | Matthews |
| 2021/0052722 A1 | 2/2021 | Walser et al. |

FOREIGN PATENT DOCUMENTS

| | | | |
|---|---|---|---|
| JP | 2009522258 | A | 6/2009 |
| JP | 2011225525 | A | 11/2011 |
| JP | 2013505897 | A | 2/2013 |
| JP | 2013519649 | A | 5/2013 |
| JP | 2014509606 | A | 4/2014 |
| WO | 199215285 | A1 | 9/1992 |
| WO | 2004075875 | A1 | 9/2004 |
| WO | 2007075171 | A1 | 7/2007 |
| WO | 2010059534 | A2 | 5/2010 |
| WO | 2010069595 | A1 | 6/2010 |
| WO | 2010059534 | A3 | 1/2011 |
| WO | 2011012990 | A2 | 2/2011 |
| WO | 2011012990 | A3 | 6/2011 |
| WO | 2011098499 | A1 | 8/2011 |
| WO | 2012001074 | A2 | 1/2012 |
| WO | 2012001074 | A3 | 3/2012 |
| WO | 2012123759 | A1 | 9/2012 |
| WO | 2013087119 | A1 | 6/2013 |
| WO | 2013087837 | A1 | 6/2013 |
| WO | 2014159607 | A1 | 10/2014 |
| WO | 2014159609 | A1 | 10/2014 |
| WO | 2015187736 | A1 | 12/2015 |
| WO | 2016033094 | A1 | 3/2016 |
| WO | 2016033094 | A9 | 8/2016 |
| WO | 2018132733 | A1 | 7/2018 |
| WO | 2018146274 | A1 | 8/2018 |
| WO | 2019089978 | A1 | 5/2019 |
| WO | 2020023925 | A1 | 1/2020 |
| WO | 2020037151 | A1 | 2/2020 |
| WO | 2020131917 | A1 | 6/2020 |
| WO | 2020132341 | A1 | 6/2020 |
| WO | 2020198024 | A1 | 10/2020 |
| WO | 2020237181 | A1 | 11/2020 |

OTHER PUBLICATIONS

Adelman, D.C. (Oct. 17, 2018). "Efficacy and Safety of AR101 in Peanut Allergy: Resultsfrom a Phase 3, Randomized, Double-Blind Placebo Controlled Trial (PALISDAE)," InternationalFood Allergy & Anaphylaxis Alliance (IFAAA) Meeting, Copenhagen, Denmark, 23 pages.

Altschul, A.S. et al. (Sep. 2001). "Manufacturing and Labeling Issues for Commercial Products: Relevance to Food Allergy," J. Allergy Clin. Immunol. 108(3):468, 1 page.

Anagnostou, K. et al. (2011). "Efficacy and Safety of High-Dose Peanut Oral Immunotherapy with Factors Predicting Outcome," Clinical & Experimental Allergy, 41:1273-1281.

Anagnostou, K. et al. (Apr. 12, 2014, e-pub. Jan. 30, 2014). "Assessing the Efficacy of Oral Immunotherapy for the Desensitization of Peanut Allergy in Children (STOP II): A Phase 2 Randomized Controlled Trial," The Lancet 383(9925):1297-1304.

Avery, N.J. et al. (Oct. 2003). "Assessment of Quality of Life in Children with Peanut Allergy," Ped. Allergy Immunol. 14(5):378-382. Abstract Only, 2 pages.

Ballmer-Weber B.K. et al. (2015). "IgE Recognition Patterns in Peanut Allergy are Age Dependent: Perspectives of the Europrevail Study," Allergy 70:391-407.

Bernard, H. et al. (2007, e-pub. Oct. 20, 2007) "Identification of a New Natural Ara h6 Isoform and of its Proteolytic Product as Major Allergens in Peanut," J. of Agricultural and Food Chem. 55(23):9663-9669.

Beyer, K et al. (Oct. 19, 2018). "Adrenaline Use and Reaction-Severity During the ExitDouble-Blind, Placebo-Controlled Food Challenge (DBPCFC) with Peanut in Subjects Aged 4-17 Years in PALISADE, a Phase 3, Randomised, Double-Blind, Placebo-Controlled Trial,"presented at the Food Allergy and Anaphylaxis Meeting (FAAM), Copenhagen Denmark, 13 pages.

Bird, A. et al. (Mar./Apr. 2018). "Efficacy and Safety of AR101 in Oral Immunotherapy for Peanut Allergy: Results of ARC001, a Randomized, Double-Blind, Placebo-Controlled Phase 2 Clinical Trial," The Journal of Allergy and Clinical Immunology: In Practice. 6(2):476-485.

Blumchen, K. et al. (Jul. 2010). "Oral Peanut Immunotherapy in Children with Peanut Anaphylaxis," J Allergy Clin Immunol. 126(1):83-91.

Bock, S.A. et al. (Dec. 1988). "Double-Blind, Placebo-Controlled Food Challenge (DBPCFC) as an Office Procedure: A Manual," J Allergy Clin Immunol. 82(6):986-997.

Bock, S.A. et al. (Jan. 2001). "Fatalities Due to Anaphylactic Reactions to Foods," J Allergy Clin. Immunol. 107(1):191-193.

Bock, S.A. et al. (Oct. 1990). "Patterns of Food Hypersensitivity During Sixteen Years of Double-Blind, Placebo-Controlled Food Challenges," J Pediatr. 117(4):561-567.

Bollinger, M.E. et al. (Mar. 2006). "The Impact of Food Allergy on the Daily Activities of Children and Their Families," Ann Allergy Asthma Immunol. 96(3):415-421. Abstract Only, 2 pages.

Bousquet, J. (2004). "Chapter 6—Primary and Secondary Prevention of Allergy and Asthma by Allergen Therapeutic Vaccines," in Allergens and Allergen Immunotherapy 18:105-114.

Boyce, J.A. et al. (Dec. 2010). "Guidelines for the Diagnosis and Management of Food Allergy in The United States: Report of the NIAID-Sponsored Expert Panel," J. Allergy and Clinical Immunology 126(6):S1-S58.

Buchanan, A.D. et al. (Jan. 2007). "Egg Oral Immunotherapy in Nonanaphylactic Children with Egg Allergy," J. Allergy Clin. Immunol. 119:199-205.

Burks, A.W. (2009). "Early Peanut Consumption: Postpone or Promote?," J. Allergy Clin.Immunol. 123(2):424-425.

Burks, A.W. et al. (Jul. 19, 2012). "Oral Immunotherapy for Treatment of Egg Allergy in Children," N. Engl. J. Med. 3673:233-243.

Burks, W. (Dec. 2000). "Diagnosis of Allergic Reactions to Food," Pediatr. Ann. 29:744-752.

Burks, W. (2004). "Chapter 17: Food Allergens," Clin. Allergy Immunol. 18:319-337.

Burks, W. (American Academy of Allergy, Asthma, and Immunology National Conference. Orlando, Florida, Mar. 6, 2012). 2012 American Academy of Allergy, Asthma & Immunology Annual Meeting. "Food Allergy" "Oral Immunotherapy for Food Allergens" "Food Allergy Guidelines" "Oral Desensitization in Patients with Food Allergy" Orlando, FL Mar. 2012, 108 pages.

Burks, W. (Apr. 2003). "Peanut Allergy: A Growing Phenomenon," J. Clin. Invest. 111(7):950-952.

Burks, W. (Jun. 2003). "Skin Manifestations of Food Allergy," Pediatrics 111(6):1617-1624.

Burks, W. (May 2002). "Current Understanding of Food Allergy," Ann. NY. Acad. Sci. 964:1-12.

Burks, W. et al. (1998). "Review Article Series II: Peanut Allergens," Allergy 53:725-730.

Burman, J. et al. (2018). "High Arachis Hypogaea Allergen 2 Immunoglobulin E Levels Predict Responses to Exposure to a Small Amount of Peanut Protein," Acta Paediatrica 107:2216, 1 page.

Careri, M. et al. (2007, e-pub. Sep. 27, 2007). "Use of Specific Peptide Biomarkers for Quantitative Confirmation of Hidden Allergenic Peanut Proteins Ara h 2 and Ara h 3/4 for Food Control by Liquid Chromatography-Tandem Mass Spectrometry," Anal. Bioanal. Chem. 389(6):1901-1907.

Carr, T.F. et al. (Feb. 2019). "Longer-Term Safety and Efficacy Measures of AR101 Oral Immunotherapy for Peanut Allergy: Results From a Phase 3 Follow-On Study," Abstract 776: J. Allergy Clin. Immunol. AB256:Abstracts, 1 page.

Chassaigne, H. et al. (2007, e-pub. May 3, 2007). "Proteomics-Based Approach to Detect and Identify Major Allergens in Processed Peanuts by Capillary LC-Q-TOF (MS/MS)," J. of Agricultural and Food Chemistry 55:4461-4473.

Chen, X. et al. (2013, e-pub. Oct. 16, 2012). "Ara h2 and Ara h6 Have Similar Allergenic Activity and are Substantially Redundant," International Archives of Allergy and Immunology 160:251-258.

(56) References Cited

OTHER PUBLICATIONS

Christensen, L.P. et al. (1995). "A Simple HPLC Method for the Isolation and Quantification of the Allergens Tuliposide A and Tulipalin A in Alstroemeria," Contact Dermatitis 32:199-203.
Clark, A.T. et al. (2009). "Successful Oral Tolerance Induction in Severe Peanut Allergy," Allergy 64:1218-1220.
Clark, A.T. et al. (Aug. 2003). "Interpretation of Tests for Nut Allergy in One ThousandPatients, In Relation to Allergy or Tolerance," Clinical and Experimental Allergy 33(8):1041-1045.
Clinical Trial (Jul. 17, 2018). "Oral Desensitization to Peanut in Peanut-Allergic Children and Adults Using Characterized Peanut Allergen OT (ARC001)," NCT01987817, 7 pages.
Clinical Trial, (Jan. 10, 2019). "PALISADE Follow-on Study (ARC004)," retrieved from https://clinicaltrials.gov/ct2/show/NCT02993107?term=ARC004&rank=1, last visited Feb. 17, 2019, 5 pages.
Curatolo, W. et al. (2011, e-pub. Feb. 18, 2011). "Effects of Food on a Gastrically Degraded Drug Azithromycin Fast-Dissolving Gelatin and HPMC Capsules," Pharmaceutical Research 28(7):1531-1539.
De Oliveira, L.C.L. et al. (2013). "The Value of Specific IgE to Peanut and its Component Arah 2 in the Diagnosis of Peanut Allergy," J. Allergy Clin. Immunol. 1(4):394-398.
Donelson, S. et al. (Feb. 2020). "Peanut Allergy Burden Survey: Comparison of Responses From Adolescents and Caregivers of Adolescents," J. Allergy Clin. Immunol. Abstract # 468, AB146 Abstracts, 1 page.
Du Toit, G. et al. (May 2018). "Efficacy and Safety of AR101 in Peanut Allergic Patients Aged 4-55: Results from an International Phase 3, Randomised, Double-Blind, Placebo ControlledTrial (PALISADE)," presented at the European Academy of Allergy and Clinical Immunology (EAACI), Munich, Germany, 12 pages.
Dunnglavin, A. et al. (Feb. 23, 2019). "163: APPEAL (Allergy to Peanuts Impacting Emotions and Life): Pan-European Results on Peanut Allergy Impact on Allergic Individuals, Parents and Caregivers," American Academy of Allergy Asthma & Immunology 2019 Annual Meeting, 1 pages.
Fernández-Rivas, M. et al. (Jun. 6-8, 2020) "PALISADE Follow-On Study (ARC004): Longer-Term Outcomes With AR101 Oral Immunotherapy for Peanut Allergy," Poster 1393, EAACI Digital Congress, 1 page.
Fiocchi, A. et al. (Jul. 2006). "Food Allergy and the Introduction of Solid Foods to Infants: A Consensus Document," Ann. Allergy Asthma Immunol. 97:10-21.
Flinterman, A.E. et al. (2006). "Determination of Number Observed-Adverse-Effect Levels and Eliciting Doses in a Representative Group Of Peanut-Sensitized Children," Journal of Allergy and Clinical Immunology 117(2):448-454.
Flinterman, A.E. et al. (2007). "Children With Peanut Allergy Recognized Predominantly Ara h2 and Ara h6, Which Remains Stable Over Time," Clin. Exp. Allergy 37:1221-1228.
Frew, A.J. (2003). "25. Immunotherapy of Allergic Disease," J. Allergy Clin. Immunol. 111(2 Suppl): S712-S719.
Fu, T.J. et al. (Jun. 19, 2013, e-pub. Apr. 8, 2013). "Impacted of Thermal Processing on ELISA Detection of Peanut Allergens," J. Agric. Food Chem. 61(24):5649-5658.
Fung, I. et al. (Jan. 8, 2013). "Relating Microarray Component Testing and Reported Food Allergy and Food-Triggered Atopic Dermatitis: A Real-World Analysis," Annals of Allergy, Asthma & Immunology, 110(3):173-177.
Grimshaw, K.E.C. et al. (2015). "Incidence and risk Factors for Food Hypersensitivity in UK Infants: Results from a Birth Cohort Study," Clin Transl Allergy 6:1, 13 pages.
Gugiu, P. et al. (Mar. 18, 2020). "One Ruler to Measure Them All: Combine Data from Multiple Forms," Clinical Outcomes, pp. 1-4.
Hofmann, A.M. et al. (Aug. 2009). "Safety of a Peanut Oral Immunotherapy Protocol in Children with Peanut Allergy," J. Allergy Clin. Immunol. 124:286-291, 14 pages.
Hourihane, J.O. et al. (2019). "OA0166—Improvements in Disease-Specific Quality of Life for Peanut-Allergic Subjects Receiving AR101 Maintenance Therapy," European Journal of Allergy and Clinical Immunology, Abstract, 1 page.
Hourihane, J.O. et al. (Jun. 1997). "Clinical Characteristic of Peanut Allergy," Clinical and Experimental Allergy 27(6):634-639.
Hourihane, J.O. et al. (Sep. 30-Oct. 2, 2018) "Abstract OP.091: Efficacy and Safety of AR101: Results of the Phase 3 Peanut Allergy Oral Immunotherapy Study for Desensitization (PALISADE) Trial," Abstracts, 2018 Annual Meeting of the British Society for Allergy and Clinical Immunology, 121 pages.
International Preliminary Report on Patentability of PCT Application PCT/US2014/024405, dated Mar. 9, 2015, filed on Mar. 12, 2014, 40 pages.
International Preliminary Report on Patentability Search Report for PCT Application PCT/US2014/024401, dated Sep. 15, 2015 10 pages.
International Preliminary Report on Patentability Search Report for PCT Application PCT/US2018/058777, dated May 5, 2020, filed Nov. 1, 2018, 17 pages.
International Preliminary Report on Patentability, dated Jun. 16, 2021 for PCT Application PCT/US2019/067634, filed Dec. 19, 2019, 9 pages.
International Preliminary Report on Patentability, dated Feb. 16, 2021, for PCT Application No. PCT/US2019/046706, filed Aug. 15, 2019, 7 pages.
International Search Report and Written Opinion for PCT Application PCT/US2014/024401, dated Jul. 21, 2014, filed Mar. 12, 2014, 13 pages.
International Search Report and Written Opinion of PCT Application PCT/US2014/024405. dated Aug. 18, 2014, 5 pages.
International Search Report and Written Opinion of the International Searching Authority, dated Feb. 22, 2019, for PCT Application No. PCT/US2018/58777, filed Nov. 1, 2018, 21 pages.
International Search Report and Written Opinion, dated Aug. 3, 2020, for PCT Application No. PCT/US2020/032179, filed May 8, 2020, 10 pages.
International Search Report and Written Opinion, dated Jun. 16, 2020, for PCT Application PCT/US2020/23903, filed Mar. 20, 2020, 9 pages.
International Search Report and Written Opinion, dated Mar. 2, 2020, for PCT Application PCT/US2019/067634, filed Dec. 19, 2019, 11 pages.
International Search Report and Written Opinion, dated Oct. 29, 2019, for PCT Application No. PCT/US2019/046706, filed Aug. 15, 2019, 13 pages.
Jones, S.M. et al. (2014). "State of the Art on Food Allergen Immunotherapy: Oral, Sublingual, and Epicutaneous," J. Allergy Clin. Immunol. 133(2):318-323.
Jones, S.M. et al. (Aug. 2009). "Clinical Efficacy and Immune Regulation with Peanut Oral Immunotherapy," J. Allergy Clin. Immunol. 124(2):292-30197, 20 pages.
Jones, S.M. et al. (Mar. 4, 2018). "Efficacy and Safety of AR101 in Peanut Allergy: Results from a Phase 3, Randomized, Double-Blind, Placebo-Controlled Trial (PALISADE)," Late-Breaking Abstract Sessions, AAAAI-WAO Joint Congress, Orlando. The Journal of Allergy and Clinical Immunology 141(2):AB412-AB414. Abstract L6, 14 pages.
Joshi, P.S. et al. (2002). "Interpretation of Commercial Food Ingredient Labels by Parents of Food-Allergic Children," J. Allergy Clin. Immunol. 109(6):1019-1021.
Kapsenberg, M.L. et al. (Jun. 1999). "The Paradigm of Type 1 and Type 2 Antigen-Presenting Cells. Implications for Atopic Allergy," Clin. Exp. Allergy 29(Suppl. 2):33-36.
Kim, E.H., et al. (Mar. 2011). "Sublingual Immunotherapy for Peanut Allergy: Clinical and Immunologic Evidence of Desensitization," J. Allergy Clin. Immunol. 127(3):640-646, 19 pages.
King, R.M. et al. (2009). "Impact of Peanut Allergy on Quality of Life, Stress and Anxiety in the Family," Allergy, 64(3):461-468, 31 pages.
Koid, A. et al. (2012). "Purified natural Ara h6: An Important Marker for IgE Response to Peanut," J. Immunology 188(1001):177. 15 Meeting Abstract Supplemental, 1 page, (Abstract Only).

(56) References Cited

OTHER PUBLICATIONS

Koid, A. et al. (Jan. 8, 2014). "Ara h 6 Complements Ara h 2 as an Important Marker for IgE Reactivity to Peanut," J. Agric. Food Chem. 62(1):206-213, 18 pages.

Koppelman et al. (Feb. 19, 1999). "Heat-Induced Conformational Changes of Ara h 1, A Major Peanut Allergen, Do not Affect its Allergenic Properties," J. Biol. Chem. 274(8):4770-4777.

Koppelman, S et al. (2012). "Abstract 1463—The Content of Allergens Arah1, Arah2, Ara h3, and Ara h6 in Different Peanut Cultivars Commonly Consumed in Europe and the USA," Allergy 67(Suppl. 96):548.

Koppelman, S.J. et al. (2001). "Quantification of Major Peanut Allergens Ara h1 and Ara h2 in the Peanut Varieties Runner, Spanish, Virginia, and Valencia, Bred in Different Parts of the World," Allergy 56:132-137.

Koppelman, S.J. et al. (2004). "Relevance of Ara h1, Ara h2, and Ara h3 in Peanut Allergic Patients, as Determined by Immunoglobulin E Western Blotting, Basophil-Histamine Release, and Intracutaneous Testing: Ara h2 is the Most Important Peanut Allergen," Clin. Exp. Allergy 34:583-590.

Koppleman, S.J. et al. (2010). "Digestion of Peanut Allergens Ara h1, Ara h3 and Ara h6: A Comparative In Vitro Study and Partial Characterization of Digestion-Resistant Peptides," Molecular Nutrition and Food Research 54:1711-1721.

Krieg, A.M. et al. (Apr. 6, 1995). "CpG Motifs in Bacterial DNA Trigger Direct B-Cell Activation," Nature 374:546-549.

Krimpenfort et al. (1988). "Transcription of T Cell Receptor β-Chain Genes is Controlled by a Downstream Regulatory Element," EMBO J. 7(3):745-750.

Kulis, et al. (Feb. 2012). The 2S Albumin Allergens of Archis Hypogaea, Ara h 2 and Ara h 6, are the Major Elicitors of Anaphylaxis and can Effectively Desensitize Peanut-Allergic Mice, Clinical & Experimental Allergy: Journal of British Society for Allergy and Clinical Immunology 42(2):326-336, 18 pages.

Lehmann, K. et al. (2006). "Structure and Stability of 2S Albumin-Type Peanut Allergens: Implications for the Severity of Peanut Allergic Reactions," Biochem. J. 395:463-472.

Lehrer, S.B. et al. (1999). "Immunotherapy for Food Allergies. Past, Present, Future," Clin. Rev. Allergy Immunol. 17(3):361-381.

Maloney, J.M. et al. (Jul. 2008, e-pub. May 27, 2008). "The Use of Serum-Specific IgE Measurements for the Diagnosis of Peanut, Tree Nut, and Seed Allergy," Journal of Allergy and Clinical Immunology 122(1):145-151.

Mondoulet et al. (Feb. 21, 2012). "Epicutaneous Immunotherapy (EPIT) Blocks the Allergic Esophago-Gastro-Enteropathy Induced by Sustained Oral Exposure to Peanuts in Sensitized Mice," Plos One 7(2):e31967, 10 pages.

Morishita M. et al. (Oct. 2006). "Is the Oral Route Possible for Peptide and Protein Drug Delivery?" Drug Discovery Today 11(19/20):905-910.

Moutete, H.F. et al. (1995)."Purification of Allergenic Proteins from Peanut for Preparation of the Reactive Solid Phase of a Specific IgE Radioimmunoassay," J. Chromatograph. B. 664:211-217.

Muheem, A. et al. (2014). "A Review on the Strategies for Oral Delivery of Proteins and Peptides and Their Clinical Perspectives," Saudi Pharmaceutical Journal, 16 pages.

Narisety, S.D. et al. (Sep. 2009). "Open-Label Maintenance After Milk Oral Immunotherapy for IgE-Mediated Cow's Milk Allergy," J. Allergy Clin. Immunol. 124(3):610-612, 6 pages.

Nelson, H.S. et al. (1997). "Treatment of Anaphylactic Sensitivity to Peanuts by Immunotherapy with Injections of Aqueous Peanut Extract," J. Allergy Clin. Immunol. 99(6 Pt 1):744-751.

Nicolaou, N. et al. (Jan. 2010). "Allergy or Tolerance in Children Sensitized to Peanut: Prevalence and Differentiation Using Component-Resolved Diagnostics," J Allergy Clin. Immunol. 125:191-197.

Nowak-Wegrzyn, A. et al. (Feb. 2020). "Peanut Allergy Burden Survey: Impact of Peanut Allergy on Global Quality of Life in Adolescent Patients," J. Allergy Clin. Immunol. Abstract # 466, AB146 Abstracts, 1 page.

Ohayon, J. et al. (Feb. 2020). "Improvements in Self-Reported Disease-Specific Quality of Life Among Peanut-Allergic Subjects Receiving AR101 for 28 or 56 Weeks Beyond the First Year of Treatment," J. Allergy Clin. Immunol. Abstract 432, AB136 Abstracts, 1 pages.

Oppenheimer, J.J. et al. (1992). "Treatment of Peanut Allergy with Rush Immunotherapy," J. Allergy Clin. Immunol. 90(2):256-262.

O'Connell. (2012). "Uses of Sieves in the Pharmaceutical Industry and the Increased Demand for Containment," International Pharmaceutical Industry 4(4):88-90.

Pajno, G.B. et al. (2014). "Oral Immunotherapy for Treatment of Immunoglobulin E-Mediated Food Allergy: The Transition to Clinical Practice," Pediatr Allergy Immunol Pulmonol. 27(2):42-50.

Peeters, K.A.B.M. et al. (2007). "Does Skin Prick Test Reactivity to Purified Allergens Correlate with Clinical Severity of Peanut Allergy?" Clinical and Experimental Allergy 37:108-115.

Pele, M. (2010). "Peanut Allergens," Romanian Biotechnological Letters 15(2):5204-5212.

Pingali, K. et al. (May 16, 2011, e-pub. Feb. 26, 2011). "Mixing Order of Glidant and Lubricant—Influence on Powder and Table Properties," Int. J. Pharm. 409:269-277, 22 pages.

Pisetsky, D.S. (Oct. 1996). "Immune Activation by Bacterial DNA: A New Genetic Code," Immunity 5:303-310.

Podczek, F. et al. (1999). "The Filling of Granules into Hard Gelatin Capsules," International Journal of Pharmaceutics 188(1):59-69.

Poms, R.E. et al. (2004). "Effect of Roasting History and Buffer Composition on Peanut Protein Extraction Efficiency," Mol. Nutr. Food Res 48:459-464.

Porterfield, H.S. et al. (Jul. 2009). "Effector Activity of Peanut Allergens: A Critical Role for Ara h2, Ara h6 and Their Variants," Clin. Exp Allergy 39(7):1099-1108, 19 pages.

Prescott, K. et al. (Mar. 2-5, 2018). "Exploration of Non-Daily Maintenance Dosing Regimens in Peanut Oral Immmunotherapy," Scientific Abstract Sessions, AAAAI-WAO Joint Congress, Orlando. The Journal of Allergy and Clinical Immunology Abstract 772,141(2):AB294-AB361, 1 page.

Project Code (2020). "Devising and Testing a Scoring Algorithm for the Food Allergy Quality of Life Questionnaire (FAQLQ) Across Multiple Forms," Clinical Outcomes pp. 1-3.

Publication Information for Burman, J. et al. (2018). "High Arachis Hypogaea Allergen 2 Immunoglobulin E Levels Predict Responses to Exposure to a Small Amount of Peanut Protein," Acta Paediatrica 107:2216, retrieved from Internet https://onlinelibrary.wiley.com/doi/abs/10.1111/apa.14511, last visited Feb. 7, 2021.

Rancé, F. et al. (Jun. 2002). "Improved Screening for Peanut Allergy by the Combined Use of Skin Prick Tests and Specific IgE Assays," Journal of Allergy and Clinical Immunology 109(6):1027-1033.

Roberts, G. et al. (Jun. 2005). "Diagnosing Peanut Allergy with Skin Prick and Specific IgE Testing," J. Allergy Clin. Immunol. 115:1291-1296.

Salvilla, S.A. et al. (May 16, 2014). "Disease-Specific Health-Related Quality of Life Instruments for IgE-Mediated Food Allergy," Allergy 69:834-844.

Sampson, H. A. et al. (2011). "A Phase II, Randomized, Double Blind, Parallel Group, Placebo Controlled Oral Food Challenge Trial of Xolair (omalizumab) in Peanut Allergy," J. Allergy Clin. Immunol. 127(5):1309-1310.

Sampson, H.A. et al. (1997). "Clinical Aspects of Allergic Disease: Relationship Between Food-Specific IgE Concentrations and the Risk of Positive Food Challenges in Children and Adolescents," J. Allergy Clin. Immunol. 100(4):444-451.

Sampson, H.A. et al. (2005). "Symposium on the Definition and Management of Anaphylaxis: Summary Report," J. Allergy Clin. Immunol. 115(3):584-591.

Santos, A.F. et al. (Sep. 2014). "Food, Drug, Insect Sting Allergy, and Anaphylaxis: Basophil Activation Test Discriminates Between Allergy and Tolerance in Peanut-Sensitized Children," J. Allergy Clin. Immunol. 134:645-652.

Schmitt, D.A. et al. (2010, e-pub. Dec. 22, 2009). "Processing can Alter the Properties of Peanut Extract Preparations," J. Agric. Food Chem. 58:1138-1143.

(56) References Cited

OTHER PUBLICATIONS

Secrist, H. et al. (Mar. 1995). "Interleukin 4 Production by CD4+ T Cells from Allergic Individuals is Modulated by Antigen Concentration and Antigen-Presenting Cell Type," J. Exp. Med. 181(3):1081-1089.
Sen, M. et al. (2002). "Protein Structure Plays a Critical Role in Peanut Allergen Stability and May Determine Immunodominant IgE-Binding Epitopes," The Journal of Immunology 169:882-887.
Sher, E. et al. (May 2018). "Efficacy and Safety of AR101 in Peanut Allergy: Results from a Phase 3, Randomized, Double-Blind Placebo Controlled Trial (PALISDAE)," presented at the Eastern Allergy Conference (EAC), Palm Beach, Florida. 1 page.
Shreffler, W.G. et al. (Apr. 2004). "Microarray immunoassay: Association of Clinical History, in vitro IgE Function, and Heterogeneity of Allergenic Peanut Epitopes," J. Allergy Clin. Immunol. 113(4):776-782.
Sicherer, S.H. (2011, e-pub. Jan. 13, 2011). "Epidemiology of Food Allergy," J. Allergy Clin. Immunol. 127(3):594-602.
Sicherer, S.H. (Nov. 1999). "Food Allergy: When and How to Perform Oral Food Challenges," Pediatr. Allergy Immunol. 10(4):226-234.
Sicherer, S.H. et al. (Feb. 2014, e-pub. Dec. 31, 2013). "Food Allergy: Epidemiology, Pathogenesis, Diagnosis, and Treatment," J. Allergy Clin. Immunol. 133:291-307.
Sicherer, S.H. et al. (Jul. 1998). "Clinical Features of Acute Allergic Reactions to Peanut and Tree Nuts in Children," Pediatrics 102(1):1-6.
Sicherer, S.H. et al. (May 2010). "Immunologic features of Infants with Milk or Egg Allergy Enrolled in an Observational Study (Consortium of Food Allergy Research) of Food Allergy)," J. Allergy Clin. Immunol. 125:1077-1083, 14 pages.
Singh, H. et al. (Oct. 2011). "Developing RP-HPLC Method for Detection of Peanut Allergens," in AACC International Annual Meeting, Oct. 16-19, 2011. Retrieved from the Internet http://www.aaccnet.org/meetings/Documents/2011Abstracts/p11ma199.htm, last visited Feb. 17, 2016, 1 page. (Abstract Only).
Skolnick, H.S. et al. (Feb. 2001). "Food and Drug Reactions and Anaphylaxis: The Natural History of Peanut Allergy," J. Allergy Clin. Immunol. 107(2):367-374.
Skripak, J.M. et al. (2009). "Mammalian Milk Allergy: Avoidance Strategies and Oral Desensitization," Curr. Opin. Allergy Clin. Immunol. 9:259-264.
Skripak, J.M. et. al. (Dec. 2008). "A Randomized, Double-Blind, Placebo-Controlled Study of Milk Oral Immunotherapy for Cow's Milk Allergy," J. Allergy Clin. Immunol. 122(6): 1154-1160, 20 pages.
Tan, S.B. et al. (1990). "Powder Flowability as an Indication of Capsule Filling Performance," International Journal of Pharmaceutics 61(1-2):145-156.
Thyagarajan, A. et al. (Feb. 2009). "Basophil Suppression in Peanut Allergic Subjects undergoing Peanut Oral Immunotherapy (OIT)," Journal of Allergy and Clinical Immunology 123:S214-S214, (Abstract Only).
Tilles, S. et al. (Mar. 2020). "Peanut Allergy Burden Survey: Correlates of Food Allergy Quality of Life Ouestionnaire—Teen Form Scores," J. Allergy Clin. Immunol. 145(2):Abstract # 469, AB147 Abstracts, 1 page.
Van Der Zee, T. et al. (Nov. 2011). "The Eliciting Dose of Peanut in Double-Blind, Placebo-Controlled Food Challenges Decreases with Increasing Age and Specific IgE Level in Children and Young Adults," J. Allergy Clin. Immunol. 128(5):1031-1036.
Van Veen, W.J. et al. (2013). "Predictive Value of Specific IgE for Clinical Peanut Allergy in Children: Relationship with Eczema, Asthma, and Setting (Primary or Secondary Care)," Clinical and Translational Allergy 3:34, 7 pages.
Vander Leek, T.K. et al. (Dec. 2000). "The Natural History of Peanut Allergy in YoungChildren and its Association with Serum Peanut-Specific IgE," J. Pediatr. 137(6):434-435.
Varshney, P. et al. (2009, e-pub. Nov. 13, 2009). "Adverse Reactions During Peanut Oral Immunotherapy Home Dosing," J. Allergy Clin. Immunol. 124(6):1351-1352, 5 pages.
Varshney, P. et al. (Mar. 2011). A Randomized Controlled Study of Peanut Oral Immunotherapy: Clinical Desensitization and Modulation of the Allergic Response, J. Allergy and Clinical Immunology 127(3):654-660.
Vereda, A. et al. (Sep. 30-Oct. 5, 2018). "Abstract 139:Efficacy and Safety of AR101: Results of the Phase 3 Peanut Allergy Oral Immunotherapy Study for Desensitization(PALISADE) Trial," Abstract: Allergy Across the Life Course—From Origins Towards Prevention, 32nd Symposium of the Collegium International Allergologium, 84 pages.
Vickery, B.P. et al. (Jan. 2013). "Peanut Oral Immunotherapy Modifies IgE and IgG4 Responses to Major Peanut Allergens," J. Allergy Clin. Immunol. 131(1):128-134.e3, 16 pages.
Vickery, B.P. et al. (Nov. 22, 2018). "AR101 Oral Immunotherapy for Peanut Allergy," The New England Journal of Medicine 379(21):1991-2001.
Vierk, K., et al. (Jun. 2002). "Recalls of Foods Containing Undeclared Allergens Reported to the US Food and Drug Administration, Fiscal Year 1999," J. Allergy Clin. Immunol. 109(6):1022-1026.
Virkud, Y.V. et al. (Mar. 2017). "Novel Baseline Predictors of Adverse Events During Oral Immunotherapy in Children with Peanut Allergy," J. Allergy Clin. Immunol 139(3):882-888.
Wainstein, B.K. et al. (Jun. 2010). "Prediction of Anaphylazis During Peanut Food Challenge: Usefulness of the Peanut Skin Prick Test (SPT) and Specific IgE Level," Pediatr. Allergy Immunol. 21(4)(Pt 1):603-611.
Wang, J. et al. (Feb. 2019). "Impact of Peanut Allergy on Quality of Life: Baseline Results from PALISADE, a Phase 3, Double-Blind, Placebo-Controlled Trial for AR101 Oral Immunotherapy," J. Allergy Clin. Immunol. 143(2):468, Abstracts AB155, 1 page.
Wang, J. et al. (Mar. 2011). "Food Allergy," J. Clinical Investigations 121(3):827-835.
Wensing, M. et al. (Dec. 2002). "The Distribution of Individual Threshold Doses Eliciting Allergic Reactions in a Population with Peanut Allergy," J Allergy Clin Immunol. 100(6):915-920.
Wilson, D.R. et al. (2005). "Sublingual Immunotherapy for Allergic Rhinitis: Systematic Review and Meta-Analysis," Allergy 60(1):4-12.
Yamamoto, S. et al. (1992). "DNA from Bacteria, but not from Vertebrates, Induces Interferons, Activates Natural Killer Cells and Inhibits Tumor Growth," Microbiol. Immunol. 36(9):983-997.
Zhuang, Y. et al. (Sep. 5, 2012). "Redefining the Major Peanut Allergens," Immunologic Research 55(1-3):125-134.
Zimmermann, S. et al. (1998). "Cutting Edge: CpG Oligodeoxynucleotides Trigger Protective and Curative Th1 Responses in Lethal Murine Leishmaniasis," J. Immunol. 160:3627-3630.

* cited by examiner

METHODS FOR IMPROVING THE QUALITY OF LIFE OF A PATIENT WITH A PEANUT ALLERGY

CROSS-REFERENCE TO RELATED APPLICATIONS

This application claims the priority benefit of U.S. Provisional Application No. 62/846,481, filed on May 10, 2019; U.S. Provisional Application No. 62/855,384, filed on May 31, 2019; and U.S. Provisional Application No. 62/967,948, filed on Jan. 30, 2020; the disclosures of which are each incorporated herein by reference for all purposes.

FIELD OF THE INVENTION

Described herein are methods for improving the quality of life of patients with a peanut allergy.

BACKGROUND OF THE INVENTION

Peanut allergy is an allergic hypersensitivity reaction of the immune system to peanut protein. Peanut allergy often develops in childhood and is usually a lifelong affliction without effective treatment. Allergic reactions to peanut can be severe and life threatening, and are a major source of severe food-induced anaphylaxis.

Peanut allergy imposes a substantial burden on individuals and their caregivers/families. The management of peanut allergy involves ongoing medical care, financial costs, and conscientious avoidance of peanut or other adherence to medical advice. These burdens can manifest in diverse manners, including as anxiety and depressive symptoms. Anxiety regarding the risk of an allergic event may result in exclusion of peanut-allergic children from social events and more. See, for example, Bollinger et al., *The impact of food allergy on the daily activities of children and their families*, Ann. Allergy Asthma Immunol. 96:415-21 (2006). Collectively, these burdens can impact an individual's quality of life (QoL), and even the quality of life of their caregivers or family members. See, for example, King et al., *Impact of peanut allergy on quality of life, stress and anxiety in the family*, Allergy, 64(3):461-8(2009). The burden experienced by individuals having a peanut allergy may be greater than the burden experienced by individuals having other serious chronic diseases, including type-1 diabetes. See, for example, Avery et al., *Assessment of quality of life in children with peanut allergy*, Ped. Allergy Immunol. 14:378-82 (2003).

The standard of care for treating peanut allergy generally includes dietary elimination and avoidance of peanuts, education on the signs of anaphylaxis, and administration of injectable epinephrine in response to severe allergic reactions with dietary exposure to peanut protein. However, accidental ingestion of peanuts is common, due to difficulty in interpreting food labels and the presence of undeclared ingredients in unlabeled food. Oral immunotherapy (OIT) is a promising new treatment for peanut allergy. See, for example, Bird et al., *Efficacy and Safety of AR101 in Oral Immunotherapy for Peanut Allergy: Results of ARC001; a randomized Double-Blind, Placebo-Controlled Phase 2 Clinical Trial*, J. Clin. Immunol. Pract., 6(2):476-485 (2018). Peanut OIT includes exposing patients to gradually increasing doses of peanut protein to induce desensitization, which is intended to reduce the risk of a serious reaction upon accidental exposure to peanut.

SUMMARY OF THE INVENTION

Described herein are methods of improving the quality of life of a patient with a peanut allergy by an oral immunotherapy according to an oral immunotherapy schedule.

In some embodiments, a method of improving the quality of life of a patient with a peanut allergy, comprises: administering to the patient a peanut composition according to an oral immunotherapy schedule.

In some embodiments, the patient is informed that the peanut composition is being administered. In some embodiments, the patient is informed that the peanut composition is being administered to the patient at the start of the oral immunotherapy schedule. In some embodiments, the patient is informed that the peanut composition is being administered to the patient during an up-dosing phase of the oral immunotherapy schedule. In some embodiments, the patient is informed that the peanut composition is being administered to the patient during a maintenance phase of the oral immunotherapy schedule.

In some embodiments, the method further comprises informing the patient that the peanut composition is being administered to the patient. In some embodiments, the patient is informed that the peanut composition is being administered to the patient prior to the start of the oral immunotherapy schedule. In some embodiments, the patient is informed that the peanut composition is being administered to the patient during an up-dosing phase of an oral immunotherapy schedule. In some embodiments, the patient is informed that the peanut composition is being administered to the patient during a maintenance phase of the oral immunotherapy schedule.

In some embodiments, the quality of life improvement is measured using a quality of life questionnaire (QoLQ). In some embodiments, the QoLQ comprises one or more scored domains of measurement. In some embodiments, the QoLQ is a Food Allergy Quality of Life Questionnaire (FAQLQ). In some embodiments, the FAQLQ is a FAQLQ-child form (FAQLQ-CF), FAQLQ-teen form (FAQLQ-TF), FAQLQ-adult form (FAQLQ-AF), or FAQLQ-parent form (FAQLQ-PF).

In some embodiments, a method of improving the quality of life of a patient with a peanut allergy, as assessed by a quality of life questionnaire (QoLQ), comprises administering to the patient a peanut composition according to an oral immunotherapy schedule. In some embodiments, the patient is informed that the peanut composition is being administered. In some embodiments, the patient is informed that the peanut composition is being administered to the patient at the start of the oral immunotherapy schedule. In some embodiments, the patient is informed that the peanut composition is being administered to the patient during an up-dosing phase of the oral immunotherapy schedule. In some embodiments, the patient is informed that the peanut composition is being administered during a maintenance phase of the oral immunotherapy schedule. In some embodiments, the method further comprises informing the patient that the peanut composition is being administered to the patient. In some embodiments, the method further comprises informing the patient that the peanut composition is being administered to the patient, and the patient is informed that the peanut composition is being administered to the patient prior to the start of the oral immunotherapy schedule. In some embodiments, the method further comprises informing the patient that the peanut composition is being administered to the patient, and the patient is informed that the peanut composition is being administered to the patient during an up-dosing phase of an oral immunotherapy schedule. In some embodiments, the method further comprises informing the patient that the peanut composition is being administered to the patient, and the patient is informed that the peanut composition is being administered to the patient during a maintenance phase of the oral immunotherapy schedule. In some embodiments, the QoLQ comprises one or more scored domains of measurement. In some embodiments, the QoLQ is a Food Allergy Quality of Life Questionnaire (FAQLQ). In some embodiments, the FAQLQ is a FAQLQ-child form (FAQLQ-CF), FAQLQ-teen form (FAQLQ-TF), FAQLQ-adult form (FAQLQ-AF), or FAQLQ-parent form (FAQLQ-PF). In some embodiments, the QoLQ is a Food Allergy Independent Measure (FAIM). In some embodiments, the FAIM is a FAIM-child form (FAIM-CF), FAIM-teen form (FAIM-TF), FAIM-adult form (FAIM-AF), or FAIM-parent form (FAIM-PF). In some embodiments, the QoLQ is a Pediatric Quality of Life Inventory (PedsQL).

In some embodiments of the preceding methods, the quality of life is improved for at least 6 months. In some embodiments, the quality of life is improved for at least 12 months.

In some embodiments, the one or more scored domains of the QoLQ are each scored on a scale between 1 and 7, or are each converted to a score between a first score and a second score, wherein the second score indicates worse quality of life. In some embodiments, an improvement in the patient's quality of life is at least 0.5 points in one or more domains of the QoLQ at a second time point after a period of oral immunotherapy as compared to an assessment at a first time point before the period of oral immunotherapy. In some embodiments, an improvement in the patient's quality of life is at least 0.5 points in a total score of the QoLQ at a second time point after a period of oral immunotherapy as compared to an assessment at a first time point before the period of oral immunotherapy; wherein the total score is the average of each domain score. In some embodiments, the period of oral immunotherapy between the first time point and the second time point is the up-dosing phase of the oral immunotherapy schedule. In some embodiments, the period of oral immunotherapy between the first time point and the second time point is at least 1 month of a maintenance therapy of the oral immunotherapy schedule.

In some embodiments, the quality of life improvement is measured using a quality of life questionnaire (QoLQ). In some embodiments, the QoLQ is a Food Allergy Independent Measure (FAIM). In some embodiments, the FAIM is a FAIM-child form (FAIM-CF), FAIM-teen form (FAIM-TF), FAIM-adult form (FAIM-AF), or FAIM-parent form (FAIM-PF). In some embodiments, an improvement in the patient's quality of life is at least 0.5 points in a total score of the QoLQ at a second time point after a period of oral immunotherapy as compared to an assessment at a first time point before the period of oral immunotherapy; wherein the total score is the average of each domain score. In some embodiments, the period of oral immunotherapy between the first time point and the second time point is the up-dosing phase of the oral immunotherapy schedule. In some embodiments, the period of oral immunotherapy between the first time point and the second time point is at least 1 month of a maintenance therapy of the oral immunotherapy schedule.

In some embodiments, the quality of life improves after 6 months of the oral immunotherapy schedule.

In some embodiments, the oral immunotherapy schedule comprises an up-dosing phase and a maintenance phase. In some embodiments, the peanut composition is administered to the patient during the maintenance phase on a daily basis. In some embodiments, the maintenance phase is at least 3 months. In some embodiments, the peanut composition is administered to the patient during a maintenance phase of the oral immunotherapy schedule at a dose of about 300 mg peanut protein or more. In some embodiments, the up-dosing phase comprises administering to the patient two or more different doses between about 3 mg and about the dose of an initial maintenance phase dose.

In some embodiments, the oral immunotherapy schedule comprises an up-dosing phase that is between about 3 months and about 2 years in length.

In some embodiments, the oral immunotherapy schedule further comprises an initial escalation phase.

In some embodiments, the patient is about 4 years old or older. In some embodiments, the patient is between about 4 years old and about 17 years old. In some embodiments, the patient is between about 8 years old and about 17 years old.

In some embodiments, the method comprises measuring the quality of life before administering to the patient a peanut composition according to an oral immunotherapy schedule. In some embodiments, the method comprises measuring the quality of life after administering to the patient a peanut composition according to an oral immunotherapy schedule. In some embodiments, the method comprises measuring the quality of life after informing the patient that the peanut composition is being administered. In some embodiments, the quality of life of the patient is improved as determined by a quality of life questionnaire (QoLQ).

DETAILED DESCRIPTION OF THE INVENTION

Figure 1:
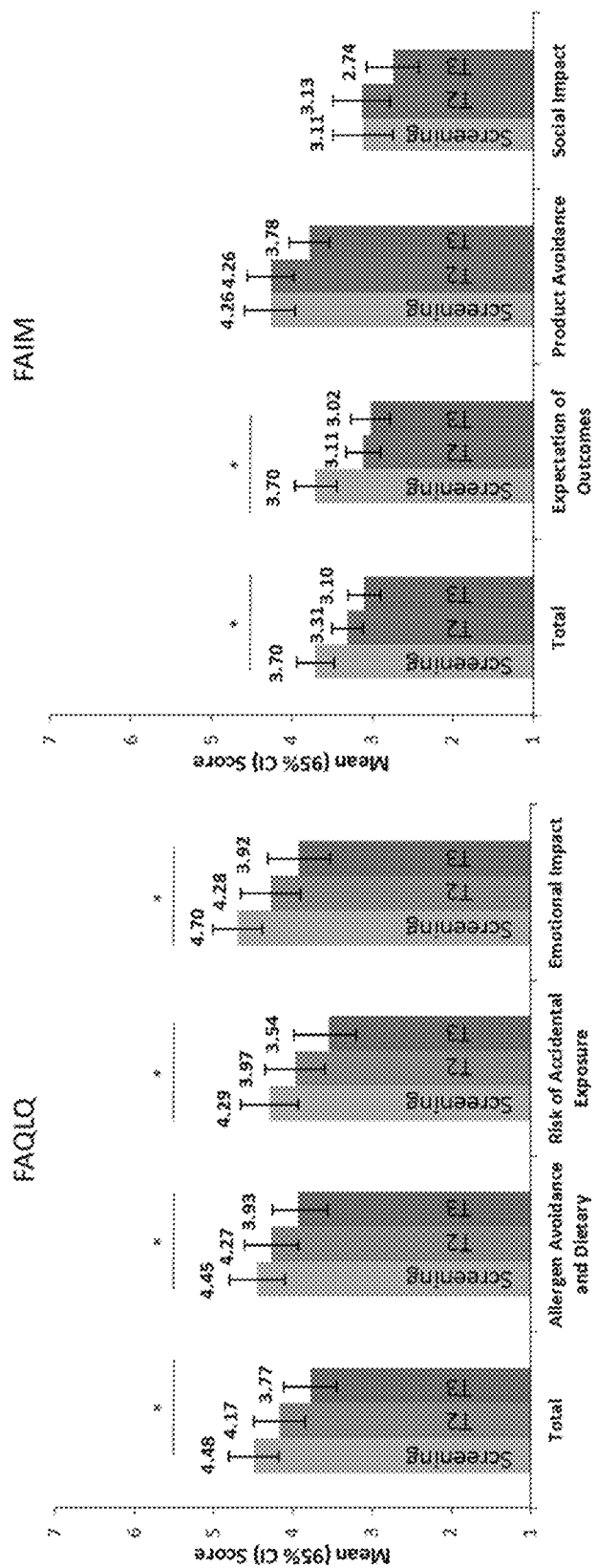
FIG. 1 shows self-reported quality of life results for subjects (ages 8-17 years) participating in two peanut OIT clinical trials (PALISADE and an open label extension of the PALISADE trial) as measured by a Food Allergy Quality of Life Questionnaire (FAQLQ; e.g., FAQLQ-CF or FAQLQ-TF) and by a Food Allergy Independent Measure (FAIM; e.g., FAIM-CF or FAIM-TF) at three time points (left: FAQLQ; right: FAIM). The first time point occurred during the screening of the first clinical trial (PALISADE). The second time point (T2) occurred after the completion of a double-blind placebo controlled food challenge (DBPCFC) administered at PALISADE exit and before the start of the open label extension. The third time point (T3) occurred at the exit of the open label extension. The left panel of FIG. 1 shows mean scores (with 95% confidence interval indicated) for the FAQLQ total score and for domains of Allergen Avoidance and Dietary Restrictions, Risk of Accidental Exposure, and Emotional Impact. The right panel of FIG. 1 shows mean scores (with 95% confidence interval indicated) for the FAIM total score and for questions of Expectation of Outcomes, Product Avoidance, and Social Impact. Both total score results and four of the six domain/question score results exceeded the threshold of the minimal clinically important difference (MCID) of 0.5 between PALISADE screening and T3, and are indicated by an asterisk above the bars.

Described herein are methods of improving the quality of life of a patient with a peanut allergy. The methods can include administering to the patient a peanut composition according to an oral immunotherapy schedule. It has been discovered that subjects who suffer a reduced quality of life as a result of a peanut allergy may have improved quality of life by treatment with a peanut composition according to an oral immunotherapy schedule. Across multiple large-scale clinical trials testing the efficacy of an investigational peanut protein oral biologic drug AR101 in oral immunotherapy, significant improvements across each of the active cohorts in subject-reported and proxy-reported quality of life were observed after initial desensitization and periods of maintenance therapy. These substantial improvements across cohorts indicate that an individual receiving the treatment described herein is likely to have an improvement in quality of life.

A subject's quality of life may be improved by informing the subject they are to be administered, or are being administered, a peanut composition according to an oral immunotherapy schedule for the treatment of peanut allergy. Knowledge of treatment with an active therapeutic (i.e., the peanut composition), as opposed to being administered a composition in a blinded study without knowledge of treatment, can result in a quality of life improvement. Oral immunotherapy involves dosing with peanut protein by the same route that accidental dietary exposure occurs (i.e., oral ingestion). Once desensitization has been achieved, oral immunotherapy may therefore provide additional certainty to the patient, and/or their caregiver, that the patient is protected from accidental exposure to peanut protein, compared to other immunotherapy methods, such as those based on dermal exposure or injection. This effect may be independent of actual desensitization. Every dose of peanut protein according to an oral immunotherapy schedule after the patient has been informed they are being administered the peanut composition may reinforce the patient's confidence that they are desensitized to accidental exposure, and thus improve the patient's quality of life over time. Thus, the methods of improving the quality of life of a patient described herein can include administering the peanut composition to patients that have knowledge of the treatment, (i.e., are informed that they are receiving the peanut composition and not a placebo). The patient may be informed of active treatment prior to the start of the oral immunotherapy schedule or during the oral immunotherapy schedule (such as during an up-dosing phase or a maintenance phase of the oral immunotherapy schedule). In some embodiments, the method includes informing the patient of active treatment (i.e., that the peanut composition is being administered to the patient).

Oral immunotherapy (OIT) is a method of inducing desensitization to an allergen in a subject by regular exposure of the subject to increasing doses of the allergen. For peanut allergy, protocols for OIT typically involve an up-dosing phase (also called a build-up phase) and a maintenance phase. The OIT can further include an initial escalation phase, although this phase is optional and not required for treatment. The initial escalation phase involves exposure to small doses of peanut protein under clinical supervision to determine the sensitivity of the patient to the peanut protein. This initial escalation phase generally occurs over the course of several (e.g., three or more) hours to two days. These small doses are increased until the subject reaches a goal dose or a highest tolerated dose for the initial escalation phase. The subject then usually begins an up-dosing phase beginning with the highest tolerated dose administered in the initial escalation phase or a slightly lower dose, and escalating through a series of doses in an up-dosing phase. Additionally, peanut OIT includes a maintenance phase involving continued administration of peanut protein for a period of time. One goal of oral immunotherapy is establishing a desensitized state, wherein the subject being treated is less likely to suffer a severe or life-threatening allergic reaction upon accidental exposure to peanut protein.

Subjects having a peanut allergy may suffer a reduced quality of life, and their quality of life may be improved by the methods described herein.

Definitions

As used herein, the singular forms "a," "an," and "the" include the plural references unless the context clearly dictates otherwise.

Reference to "about" a value or parameter herein includes (and describes) variations that are directed to that value or parameter per se. For example, description referring to "about X" includes description of "X".

The term "desensitized" is used herein to refer to an increased reaction threshold to a food allergen by a subject as a result of an oral immunotherapy for the food allergen. Desensitization to a food allergen can be tested using methods known in the art, including an oral food challenge. Desensitization may be partial, wherein the subject tolerates an increased amount of the food allergen compared to prior to treatment, but still reacts to higher doses of the food allergen; or the desensitization may be complete, wherein the patient tolerates all tested doses of the food allergen.

The phrase "quality of life" as used herein is synonymous with "disease-related quality of life" and "health-related quality of life," and refers to the portion(s) of a subject's life affected by a food allergy and/or affected by its treatment.

The terms "effective," "efficacy," or "effectiveness" are used herein to refer to the ability of a therapy to induce immune modulation, such as desensitization, or sustain a desired immune state, such as a desensitized state, unless otherwise indicated.

As used herein, "maintenance phase" refers to a phase of a peanut protein oral immunotherapy that includes administration of peanut protein (i.e., a maintenance dose) to the patient, and occurs after completion of the up-dosing phase.

As used herein, a "mild allergic adverse event" refers to an observed or experienced OIT-treatment-related allergic adverse event associated with transient discomfort, but does not require immediate medical intervention such as hospitalization or epinephrine, and does not substantially interfere with daily activities.

As used herein, a "moderate allergic adverse event" refers to an observed or experienced OIT-treatment-related allergic adverse event that is associated with discomfort of a sufficient degree to interfere with daily activities and that may prompt medical intervention and/or additional observation.

As used herein, "daily" dosing means administering a dose on each consecutive calendar day. The dose may be administered as a single portion on the calendar day, or subdivided into multiple portions administered within the same calendar day.

As used herein, the phrase "serious allergic adverse event" refers to an observed or experienced OIT-treatment-related allergic adverse event leading to anaphylaxis that requires hospitalization and/or administration of epinephrine or other life-saving medical intervention.

The term "subject" or "patient" is used synonymously and interchangeably herein to describe a human of any age.

A subject "tolerates" a dose when the dose is administered to the subject without any moderate or severe allergic adverse event. A subject is considered to tolerate the dose even if a mild allergic adverse event is observed or experienced.

The terms "treat," "treating," and "treatment" are used synonymously herein to refer to any action providing a benefit to a subject afflicted with a disease state or condition, including improvement in the condition through lessening, inhibition, suppression, or elimination of at least one symptom; delay in progression of the disease; delay in recurrence of the disease; inhibition of the disease; or partially or fully reducing a response or reaction to an allergen.

An "up-dosing phase" refers to a phase of an oral immunotherapy characterized by a series of increasing food allergen doses, beginning with administration of a dose of food allergen lower than the highest dose administered to the patient during the oral immunotherapy, and ending when the highest dose administered to the patient during the oral immunotherapy is achieved.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The disclosures of all publications, patents, and patent applications referred to herein are each hereby incorporated by reference in their entireties. To the extent that any reference incorporated by reference conflicts with the instant disclosure, the instant disclosure shall control.

Methods of Improving Quality of Life

The quality of life of a patient having a peanut allergy may be improved by administering to the patient a peanut composition according to an oral immunotherapy schedule. In some embodiments, the quality of life of a patient having a peanut allergy may be improved by informing the patient that they are being administered, or going to be administered, a peanut composition according to an oral immunotherapy schedule. In some embodiments, the quality of life of a patient having a peanut allergy may be improved by instructing the patient's caregiver to inform the patient that they are being, or going to be, administered a peanut composition according to an oral immunotherapy schedule.

The subject may be informed they are to be administered, or are being administered, a peanut composition according to an oral immunotherapy schedule, or the subject's caregiver may be informed that the subject is to be administered, or is being administered, a peanut composition according to an oral immunotherapy schedule, at any time before or during the oral immunotherapy. In some embodiments, the subject is informed, or the subject's caregiver is instructed to inform the subject, before the beginning of the oral immunotherapy schedule. In some embodiments, the subject is informed, or the subject's caregiver is instructed to inform the subject, before the initiation of the up-dosing phase of the oral immunotherapy schedule. In some embodiments, the subject is informed, or the subject's caregiver is instructed to inform the subject, during the up-dosing phase of the oral immunotherapy schedule. In some embodiments, the subject is informed, or the subject's caregiver is instructed to inform the subject, after the up-dosing phase of the oral immunotherapy schedule. In some embodiments, the subject is informed, or the subject's caregiver is instructed to inform the subject, during a maintenance phase of the oral immunotherapy schedule. In some embodiments, the subject is informed, or the subject's caregiver is instructed to inform the subject, after at least a month of maintenance therapy of the oral immunotherapy schedule, such as at least 2 months, at least 3 months, at least 6 months, and at least 12 months of maintenance therapy of the oral immunotherapy.

Before, during, or after an oral immunotherapy, a subject may undergo a quality of life assessment. Peanut allergy affects quality of life through allergic reactions to peanut protein. However, even absent allergic reactions, subjects having a peanut allergy suffer impaired quality of life, including from the fear of allergic reactions, the financial burden of the allergy, the social restrictions of the allergy, and more. Subjects and their caregivers must devote significant time vetting and validating food selections, for example by reading food labels, inquiring of ingredients in unlabeled food, or avoiding food prepared in environments with potential cross-contamination. Subjects and their caregivers may experience anxiety over these burdens, which can manifest further as depressive symptoms. Subjects may avoid living alone or even eating alone for fear of a rapid onset allergic reaction. Together, these effects reduce a subject's quality of life.

Methods of measuring quality of life, such as disease-related QoL, before, during, or after OIT have been, and may be, developed and validated for the measurement of quality of life in subjects with a food allergy, such as a peanut allergy. The most common methods of assessing quality of life employ questionnaires designed to assess one or more domains, across one or more issues each, of the burden imposed by food allergy, such as peanut allergy, in qualitative and/or quantitative terms. Exemplary questionnaires are generally (1) valid, meaning that the part(s) of quality of life that are being measured relate to the food allergy; (2) reproducible, meaning that questionnaires taken under similar conditions are equivalent, and may generally produce similar results absent a change in the food allergy burden or treatment burden; (3) responsive, meaning that changes in the food allergy burden and/or treatment burden are detected and/or detectible; and (4) interpretable, meaning that scored changes are clinically significant, as determined by the questionnaire's minimal clinical important difference (MCID).

An improvement in a subject's quality of life involves a change between at least two points in time. Further, an improvement is understood with respect to a particular instrument (such as a particular quality of life questionnaire or other QoL assessment). For example, if a subject's quality of life is assessed by a quality of life questionnaire, then an improvement is an improvement in the score of that same quality of life questionnaire, such as an improvement in a particular domain or an improvement in the total score of said questionnaire. In some embodiments, the improvement is clinically significant, such as equal to or greater than the questionnaire's minimal clinical important difference (MCID). In some embodiments, the improvement is a change in a domain score, or a total score, of a quality of life questionnaire between one time point, such as a baseline measurement, to a second time point.

In some embodiments. a skilled medical provider, such as a physician, nurse, allergist, or other professional trained in the field of allergy treatment, may select a QoL assessment instrument appropriate for a subject to be treated, or being treated, by an oral immunotherapy for a food allergy, such as a peanut allergy. Preferably, QoL assessment instruments are age-appropriate and validated for the particular age range of the subject. For young subjects, a proxy-report (such as one to be completed by the subject's caregiver regarding the subject having a peanut allergy) may be required or may compliment a self-report, for example in subjects under the age of 12. For subjects 6-, 7-, or 8-years-old or older, a self-report alone may be, but is not always, sufficient. In some embodiments, assessment instruments may be validated for the native language of the subject (for self-reports) and/or the subject's caregiver (for proxy-reports). In some embodiments, assessment instruments may be culturally validated, for example, validated in the country or region where the subject (for self-reports) and/or the subject's caregiver (for proxy-reports) reside.

In some embodiments, quality of life may be assessed by quality of life questionnaires (QoLQ), such as food allergy-specific QoLQs. In some embodiments, the food allergy-specific QoLQ is a peanut allergy-specific QoLQ. A QoLQ is typically divided into one or more domains, wherein each domain relates to a category of physical, mental, emotional, or social functioning or well-being. The domains of a QoLQ may comprise one or more issues. The QoLQ may score one or more domains and/or one or more issues, individually and/or in the aggregate. Exemplary domains and/or issues covered may include, but are not limited to: bullying, teasing, family, family events, school, school events, social, social events, field trips, parties, sleepovers, playing at friends' houses, time employed to prepare foods, physical state, mental state, emotional state, expectations of outcome, perceived risk, parental anxiety, parental distress, psychosocial impact, parental coping, family support, social precaution, food allergen identification, emotional impact, food-related anxiety, social restrictions, allergen avoidance, dietary restriction, risk of accidental exposure, fear, perception, independence, and/or burden of carrying adrenaline. In some embodiments, the domain and/or issues measured by the QoLQ comprise any domain and/or issue validated to relate to the burden of having a food allergy and/or the treatment of a food allergy. In some embodiments, the domain and/or issues measured by the QoLQ comprise any domain and/or issue validated to relate to the burden of having a food allergy that is a peanut allergy and/or the treatment of a food allergy that is a peanut allergy.

In some embodiments, quality of life of a subject having a peanut allergy may be assessed by administering one or more QoLQs to a subject having a peanut allergy to measure said subject's quality of life. In some embodiments, quality of life of a subject having a peanut allergy may be assessed by proxy by administering one or more QoLQs to a subject's caregiver to measure said subject's quality of life. In some embodiments, quality of life of a subject having a peanut allergy may be assessed by administering one or more QoLQs to a subject having a peanut allergy and by administering one or more QoLQs to a subject's caregiver to measure said subject's quality of life. In some embodiments, a subject's caregiver is any individual aware of the physiological, emotional, financial, and/or physical burden of a peanut allergy on said subject. In some embodiments, a subject's caregiver is a family member (such as a parent, grandparent, sibling, aunt, uncle, cousin, etc.) or other guardian (such as a legally appointed guardian).

In some embodiments, the quality of life of a subject having a peanut allergy may be assessed by administering one or more QoLQs to measure a subject's quality of life. In some embodiments, the one or more QoLQs to measure a subject's quality of life comprise one or more QoLQs selected from: the Food Allergy Quality of Life-Parental Burden questionnaire (FAQL-PB), the Food Allergy Impact Scale (FAIS), the Food Allergy Independent Measure (FAIM), the Food Allergy Independent Measure child form (FAIM-CF), the Food Allergy Independent Measure teen form (FAIM-TF), the Food Allergy Independent Measure adult form (FAIM-AF), the Food Allergy Independent Measure parent form (FAIM-PF), the Food Allergy Parent Questionnaire (FAPQ), the Child Health Questionnaire Parental Form (CHQ-PF), the Food Allergy Self-Efficacy Scale for Parents (FASE-P), the Pediatric Allergic Disease Quality of Life Questionnaire (PADQLQ), the Food Allergy Quality of Life Questionnaire-Parent Form (FAQLQ-PF), the Food Allergy Quality of Life Questionnaire-Child Form (FAQLQ-CF), the Food Allergy Quality of Life Questionnaire-Teenager Form (FAQLQ-TF), the Food Allergy Quality of Life Assessment Tool for Adolescents (FAQL-teen), the You and Your Food Allergy questionnaire, the Food Allergy Quality of Life Questionnaire-Adult Form (FAQLQ-AF), the 36-Item Short Form Health Survey (SF-36), a EuroQol EQ-5D, such as the EuroQol 5D Youth (EQ-5D-Y) or 5-level EQ-5D (EQ-5D-5L), the Hospital Anxiety and Depression Scale (HADS), the Allergy to Peanuts ImPacting Emotions and Life (APPEAL) survey, and the Pediatric Quality of Life Inventory (PedsQL). In some embodiments, the one or more QoLQs comprise a FAQLQ, such as FAQLQ-CF, FAQLQ-TF, FAQLQ-AF, or FAQLQ-PF. In some embodiments, the one or more QoLQs comprises a self-reported FAQLQ-CF, FAQLQ-TF, or FAQLQ-AF. In some embodiments, the one or more QoLQs comprises a proxy-reported FAQLQ-PF. In some embodiments, the one or more QoLQs comprise a self-reported FAQLQ-CF, FAQLQ-TF, FAQLQ-AF and a proxy-reported FAQLQ-PF. In some embodiments, the one or more QoLQs comprise a FAIM, such as a FAIM-CF, FAIM-TF, FAIM-AF, or FAIM-PF.

A QoLQ typically comprises one or more scored domains, with each domain reflecting an aspect or category related to a subject's quality of life. In some embodiments, the QoLQ will assign a numerical score to each domain along a scale. Scores may be on any scale, with a first score associated with a better quality of life and a second score associated with a worse quality of life. For example, the scale may be between 1 and 5, between 1 and 6, between 1 and 7, or any other selected values. In accordance with some scales, a higher score can be used to indicate a worse quality of life. A total score, an aggregate score, and/or a multi-domain score may also be assessed based on the averaged score of a plurality of domains of a QoLQ. In some embodiments, a domain and/or total score of a QoLQ may be converted to a common scale, such as a score between 1 and 7, wherein 7 is associated with worse quality of life, or a score between a first score and a second score, wherein a second score is associated with worse quality of life.

The QoLQ administered should be suitable to the subjects and/or their caregivers. In some embodiments, the one or more QoLQs administered are translated to a language understood by the subject and/or their caregiver. In some embodiments, the one or more QoLQs administered are validated to ensure lingual and cultural suitability for the subject and/or their caregiver.

In some embodiments, the quality of life of a subject is assessed, at least in part, by proxy by administering a QoLQ regarding the subject to the subject's caregiver. In some embodiments, the QoLQ administered to a subject's caregiver to assess the subject's QoL is a QoLQ designed for proxy assessment of a subject having a food allergy, such as a peanut allergy. In a non-limiting exemplary embodiment, the QoLQ administered to a subject's caregiver to assess the subject's QoL by proxy is the FAQLQ-PF.

The quality of life of a subject having a peanut allergy may be improved by administering a peanut composition to the subject according to an oral immunotherapy schedule and/or informing the subject they are to be administered, or are being administered, a peanut composition according to an oral immunotherapy schedule. Said improvement in the subject's quality of life may persist (including continuing to further improve) for a period of time after the improvement as the subject continues to be administered (and/or is aware that they will continue to be administered) a peanut composition according to an oral immunotherapy schedule. The improvement may persist, including continuing to improve, even if the subject's physiological sensitivity to peanut protein does not further improve. Thus, in some embodiments, the subject's quality of life is improved for at least any of about 1 month, 3 months, 6 months, 9 months, 12 months, 18 months, 24 months, 36 months, 48 months, or 60 months. In some embodiments, the subject's quality of life is improved for at least any of about 1 month, 3 months, 6 months, 9 months, 12 months, 18 months, 24 months, 36 months, 48 months, or 60 months while the subject continues to be administered a peanut composition according to an oral immunotherapy schedule. In some embodiments, the subject's quality of life is improved for at least any of about 1 month, 3 months, 6 months, 9 months, 12 months, 18 months, 24 months, 36 months, 48 months, or 60 months after the subject has achieved a peak desensitization to peanut protein (such as by measured by an oral food challenge).

In some embodiments, the quality of life of a subject having a peanut allergy is improved by administering a peanut composition to the subject according to an oral immunotherapy schedule and/or informing the subject they are to be administered, or are being administered, a peanut composition according to an oral immunotherapy schedule. In some embodiments, the improvement in quality of life is determined by improvement in one or more domains of one or more QoLQs, wherein each domain is scored. In some embodiments, the score for each domain is converted to a score between a first score and a second score, wherein the second score indicates a worse quality of life. In some embodiments, quality of life is assessed at a first time point and a second time point. In some embodiments, the improvement in quality of life of the subject between the first time point and the second time point is at least a minimal clinically important difference. In some embodiments, the first time point is before the oral immunotherapy. In some embodiments, the first time point is before the up-dosing phase of the oral immunotherapy. In some embodiments, the first time point is during the up-dosing phase of the oral immunotherapy. In some embodiments, the first time point is during the maintenance phase of the oral immunotherapy. In some embodiments, the subject is informed that they are to be administered a peanut composition according to an oral immunotherapy schedule before the first time point. In some embodiments, the subject is informed that they are to be administered a peanut composition according to an oral immunotherapy schedule at the first time point. In some embodiments, a period of oral immunotherapy between the first time point and the second time point comprises the up-dosing phase of the oral immunotherapy schedule. In some embodiments, a period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the improvement in quality of life is determined by improvement in one or more domains of one or more QoLQs, wherein each domain is scored. In some embodiments, at least one domain is a measure of anxiety. In some embodiments, at least one domain is a measure of emotional impact, such as the emotional impact of having an allergy and/or the emotional impact of the treatment of an allergy. In some embodiments, at least one domain is a measure of social impact, such as limitations of social interaction and/or participation. In some embodiments, at least one domain is a measure of dietary impact, such as caloric intake, dietary diversity, and/or dietary exclusion. In some embodiments, at least one domain is a measure of expectations, such as expectations of treatment success and/or expectations regarding the future incidence of allergic reactions and/or expectations regarding the improvement of the disease condition. In some embodiments, the score for each domain is converted to a score between a first score and a second score, wherein the second score indicates a worse quality of life. In some embodiments, quality of life is assessed at a first time point and a second time point. In some embodiments, the score at the first time point is equal to or greater than the mid-point of the scale. For example, in an exemplary embodiment, each domain is scored on a scale from 1 to 7, wherein 7 indicates a worse quality of life, and the score of one or more domains at the first time point is equal to or greater than the mid-point of the scale, which is equal to or greater than 4. In some embodiments, the score of one or more domains at the second time point is less than the mid-point of the scale. For example, in an exemplary embodiment, each domain is scored on a scale from 1 to 7, wherein 7 indicates a worse quality of life, and the score of one or more domains at the second time point is less than the mid-point of the scale, which is less than 4. In some embodiments, the first time point is before the oral immunotherapy. In some embodiments, the first time point is before the up-dosing phase of the oral immunotherapy. In some embodiments, the first time point is during the up-dosing phase of the oral immunotherapy. In some embodiments, the first time point is during the maintenance phase of the oral immunotherapy. In some embodiments, the subject is informed that they are to be administered a peanut composition according to an oral immunotherapy schedule before the first time point. In some embodiments, the subject is informed that they are to be administered a peanut composition according to an oral immunotherapy schedule at the first time point. In some embodiments, a period of oral immunotherapy between the first time point and the second time point comprises the up-dosing phase of the oral immunotherapy schedule. In some embodiments, a period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is improved by administering a peanut composition to the subject according to an oral immunotherapy schedule and/or informing the subject they are to be administered, or are being administered, a peanut composition according to an oral immunotherapy schedule. In some embodiments, the improvement in quality of life is determined by improvement in the total score of one or more QoLQs, wherein the total score is the average of one or more domains of a QoLQ. In some embodiments, the total score is converted to a score between a first score and a second score, wherein the second score indicates a worse quality of life. In some embodiments, quality of life is assessed at a first time point and a second time point. In some embodiments, the improvement in quality of life of the subject between the first time point and the second time point is at least a minimal clinically important difference. In some embodiments, the first time point is before the oral immunotherapy. In some embodiments, the first time point is before the up-dosing phase of the oral immunotherapy. In some embodiments, the first time point is during the up-dosing phase of the oral immunotherapy. In some embodiments, the first time point is during the maintenance phase of the oral immunotherapy. In some embodiments, the subject is informed that they are to be administered a peanut composition according to an oral immunotherapy schedule before the first time point. In some embodiments, the subject is informed that they are to be administered a peanut composition according to an oral immunotherapy schedule at the first time point. In some embodiments, a period of oral immunotherapy between the first time point and the second time point comprises the up-dosing phase of the oral immunotherapy schedule. In some embodiments, a period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the improvement in quality of life is determined by improvement in the total score of one or more QoLQs, wherein the total score is the average of one or more domains of a QoLQ. In some embodiments, the total score is converted to a score between a first score and a second score, wherein the second score indicates a worse quality of life. In some embodiments, quality of life is assessed at a first time point and a second time point. In some embodiments, the score at the first time point is equal to or greater than the mid-point of the scale. For example, in an exemplary embodiment, the total score is scored on a scale from 1 to 7, wherein 7 indicates a worse quality of life, and the total score at the first time point is equal to or greater than the mid-point of the scale, which is equal to or greater than 4. In some embodiments, the total score at the second time point is less than the mid-point of the scale. For example, in an exemplary embodiment, each domain is scored on a scale from 1 to 7, wherein 7 indicates a worse quality of life, and the score of one or more domains at the second time point is less than the mid-point of the scale, which is less than 4. In some embodiments, the first time point is before the oral immunotherapy. In some embodiments, the first time point is before the up-dosing phase of the oral immunotherapy. In some embodiments, the first time point is during the up-dosing phase of the oral immunotherapy. In some embodiments, the first time point is during the maintenance phase of the oral immunotherapy. In some embodiments, the subject is informed that they are to be administered a peanut composition according to an oral immunotherapy schedule before the first time point. In some embodiments, the subject is informed that they are to be administered a peanut composition according to an oral immunotherapy schedule at the first time point. In some embodiments, a period of oral immunotherapy between the first time point and the second time point comprises the up-dosing phase of the oral immunotherapy schedule. In some embodiments, a period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAQLQ-CF. In some embodiments, the total score of a FAQLQ-CF administered to a subject having a peanut allergy at a first time point before an oral immunotherapy or during the up-dosing phase of an oral immunotherapy is 4 or higher. In some embodiments, the score of one or more domains of a FAQLQ-CF administered to a subject having a peanut allergy at a first time point before an oral immunotherapy or during the up-dosing phase of an oral immunotherapy is 4 or higher, such as a score of 4 or higher in the Allergen Avoidance and Dietary Restrictions domain, a score of 4 or higher in the Emotional Impact domain, and/or a score of 4 or higher in the Risk of Accidental Exposure domain. In some embodiments, the total score of a FAQLQ-CF administered to a subject with a peanut allergy after at a second time point after a period of oral immunotherapy as compared to the total score of a FAQLQ-CF administered to said subject at a first time point before the oral immunotherapy is improved by at least 0.5 points, such as at least 1 point, at least 2 points, at least 3 points, or at least 4 points. In some embodiments, the total score of a FAQLQ-CF administered to a subject with a peanut allergy at a second time point after a period of oral immunotherapy as compared to the total score of a FAQLQ-CF administered to said subject at a first time point during the up-dosing phase of an oral immunotherapy is improved by at least 0.5 points, such as at least 1 point, at least 2 points, at least 3 points, or at least 4 points. In some embodiments, the score of a domain of a FAQLQ-CF administered to a subject having a peanut allergy is improved by at least 0.5 points, such as at least 0.5 points in the Allergen Avoidance and Dietary Restrictions domain, at least 0.5 points in the Emotional Impact domain, and/or at least 0.5 points in the Risk of Accidental Exposure domain at a second time point after a period of oral immunotherapy as compared to the score in each domain at the first time point before the oral immunotherapy or during the up-dosing phase of the oral immunotherapy. In some embodiments, the subject is informed they are to be administered a peanut composition before the oral immunotherapy. In some embodiments, the period of oral immunotherapy between the first time point and the second time point comprises an up-dosing phase. In some embodiments, the period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAQLQ-CF. In some embodiments, the total score of a FAQLQ-CF administered to a subject having a peanut allergy at a first time point before being informed they are to be administered, or are being administered, a peanut composition according to an oral immunotherapy schedule is 4 or higher. In some embodiments, the score of one or more domains of a FAQLQ-CF administered to a subject having a peanut allergy at a first time point before being informed they are to be administered, or are being administered, a peanut composition according to an oral immunotherapy schedule is 4 or higher, such as a score of 4 or higher in the Allergen Avoidance and Dietary Restrictions domain, a score of 4 or higher in the Emotional Impact domain, and/or a score of 4 or higher in the Risk of Accidental Exposure domain. In some embodiments, the total score of a FAQLQ-CF administered to a subject with a peanut allergy at a second time point after a period after being informed they are to be administered, or are being administered, a peanut composition according to an oral immunotherapy schedule as compared to the total score of a FAQLQ-CF administered to said subject at a first time point before being informed is improved by at least 0.5 points, such as at least 1 point, at least 2 points, at least 3 points, or at least 4 points. In some embodiments, the score of a domain of a FAQLQ-CF administered to a subject having a peanut allergy is improved by at least 0.5 points, such as at least 0.5 points in the Allergen Avoidance and Dietary Restrictions domain, at least 0.5 points in the Emotional Impact domain, and/or at least 0.5 points in the Risk of Accidental Exposure domain at a second time point after being informed they are to be administered, or are being administered, a peanut composition according to an oral immunotherapy schedule as compared to the score in each domain at a time point before being informed. In some embodiments, the period of oral immunotherapy between a first time point and a second time point is at least one month of therapy. In some embodiments, the period between a first time point and a second time point comprises an up-dosing phase of the oral immunotherapy. In some embodiments, the period of oral immunotherapy between a first time point and a second point is at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAQLQ-TF. In some embodiments, the total score of a FAQLQ-TF administered to a subject having a peanut allergy at a first time point before an oral immunotherapy or during the up-dosing phase of an oral immunotherapy is 4 or higher. In some embodiments, the score of one or more domains of a FAQLQ-TF administered to a subject having a peanut allergy at a first time point before an oral immunotherapy or during the up-dosing phase of an oral immunotherapy is 4 or higher, such as a score of 4 or higher in the Allergen Avoidance and Dietary Restrictions domain, a score of 4 or higher in the Emotional Impact domain, and/or a score of 4 or higher in the Risk of Accidental Exposure domain. In some embodiments, the total score of a FAQLQ-TF administered to a subject with a peanut allergy at a second time point after a period of oral immunotherapy as compared to the total score of a FAQLQ-TF administered to said subject at a first time point before the oral immunotherapy is improved by at least 0.5 points, such as at least 1 point, at least 2 points, at least 3 points, or at least 4 points. In some embodiments, the total score of a FAQLQ-TF administered to a subject with a peanut allergy at a second time point after a period of oral immunotherapy as compared to the total score of a FAQLQ-TF administered to said subject at a first time point during the up-dosing phase of an oral immunotherapy is improved by at least 0.5 points, such as at least 1 point, at least 2 points, at least 3 points, or at least 4 points. In some embodiments, the score of a domain of a FAQLQ-TF administered to a subject having a peanut allergy is improved by at least 0.5 points, such as at least 0.5 points in the Allergen Avoidance and Dietary Restrictions domain, at least 0.5 points in the Emotional Impact domain, and/or at least 0.5 points in the Risk of Accidental Exposure domain at a second time point after a period of oral immunotherapy as compared to the score in each domain at a first time point before the oral immunotherapy or during the up-dosing phase of the oral immunotherapy. In some embodiments, the subject is informed they are to be administered a peanut composition before the oral immunotherapy. In some embodiments, the period of oral immunotherapy between the first time point and the second time point comprises an up-dosing phase. In some embodiments, the period of oral immunotherapy between a first time point and a second time point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAQLQ-TF. In some embodiments, the total score of a FAQLQ-TF administered to a subject having a peanut allergy at a first time point before being informed they are to be administered, or are being administered, a peanut composition according to an oral immunotherapy schedule is 4 or higher. In some embodiments, the score of one or more domains of a FAQLQ-TF administered to a subject having a peanut allergy at a first time point before being informed they are to be administered, or are being administered, a peanut composition according to an oral immunotherapy schedule is 4 or higher, such as a score of 4 or higher in the Allergen Avoidance and Dietary Restrictions domain, a score of 4 or higher in the Emotional Impact domain, and/or a score of 4 or higher in the Risk of Accidental Exposure domain. In some embodiments, the total score of a FAQLQ-TF administered to a subject with a peanut allergy at a second time point after a period after being informed they are to be administered, or are being administered, a peanut composition according to an oral immunotherapy schedule as compared to the total score of a FAQLQ-TF administered to said subject at a first time point before being informed is improved by at least 0.5 points, such as at least 1 point, at least 2 points, at least 3 points, or at least 4 points. In some embodiments, the score of a domain of a FAQLQ-TF administered to a subject having a peanut allergy is improved by at least 0.5 points, such as at least 0.5 points in the Allergen Avoidance and Dietary Restrictions domain, at least 0.5 points in the Emotional Impact domain, and/or at least 0.5 points in the Risk of Accidental Exposure domain at a second time point after being informed they are to be administered, or are being administered, a peanut composition according to an oral immunotherapy schedule as compared to the score in each domain at a first time point before being informed. In some embodiments, the period of oral immunotherapy between a first time point and a second time point is at least one month of oral immunotherapy. In some embodiments, the period between the first time point and the second time point comprises an up-dosing phase of the oral immunotherapy. In some embodiments, the period of oral immunotherapy between the first time point and the second point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAQLQ-AF. In some embodiments, the total score of a FAQLQ-AF administered to a subject having a peanut allergy at a first time point before an oral immunotherapy or during the up-dosing phase of an oral immunotherapy is 4 or higher. In some embodiments, the score of one or more domains of a FAQLQ-AF administered to a subject having a peanut allergy at a first time point before an oral immunotherapy or during the up-dosing phase of an oral immunotherapy is 4 or higher, such as a score of 4 or higher in the Allergen Avoidance and Dietary Restrictions domain, a score of 4 or higher in the Emotional Impact domain, a score of 4 or higher in the Food Allergy Related Health domain, and/or a score of 4 or higher in the Risk of Accidental Exposure domain. In some embodiments, the total score of a FAQLQ-AF administered to a subject with a peanut allergy at a second time point after a period of oral immunotherapy as compared to the total score of a FAQLQ-AF administered to said subject at a first time point before the oral immunotherapy is improved by at least 0.5 points, such as at least 1 point, at least 2 points, at least 3 points, or at least 4 points. In some embodiments, the total score of a FAQLQ-AF administered to a subject with a peanut allergy at a second time point after a period of oral immunotherapy as compared to the total score of a FAQLQ-AF administered to said subject at a first time point during the up-dosing phase of an oral immunotherapy is improved by at least 0.5 points, such as at least 1 point, at least 2 points, at least 3 points, or at least 4 points. In some embodiments, the score of a domain of a FAQLQ-AF administered to a subject having a peanut allergy is improved by at least 0.5 points, such as at least 0.5 points in the Allergen Avoidance and Dietary Restrictions domain, at least 0.5 points in the Emotional Impact domain, at least 0.5 points in the Food Allergy Related Health domain, and/or at least 0.5 points in the Risk of Accidental Exposure domain at a second time point after a period of oral immunotherapy as compared to the score in each domain at a first time point before the oral immunotherapy or during the up-dosing phase of the oral immunotherapy. In some embodiments, the subject is informed they are to be administered a peanut composition before the oral immunotherapy. In some embodiments, the period of oral immunotherapy between the first time point and the second time point comprises an up-dosing phase of the oral immunotherapy. In some embodiments, the period of oral immunotherapy between the first time point and the second point is at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAQLQ-AF. In some embodiments, the total score of a FAQLQ-TF administered to a subject having a peanut allergy at a first time point before being informed they are to be administered, or are being administered, a peanut composition according to an oral immunotherapy schedule is 4 or higher. In some embodiments, the score of one or more domains of a FAQLQ-AF administered to a subject having a peanut allergy at a first time point before being informed they are to be administered, or are being administered, a peanut composition according to an oral immunotherapy schedule is 4 or higher, such as a score of 4 or higher in the Allergen Avoidance and Dietary Restrictions domain, a score of 4 or higher in the Emotional Impact domain, a score of 4 or higher in the Food Allergy Related Health domain, and/or a score of 4 or higher in the Risk of Accidental Exposure domain. In some embodiments, the total score of a FAQLQ-AF administered to a subject with a peanut allergy at a second time point after a period after being informed they are to be administered, or are being administered, a peanut composition according to an oral immunotherapy schedule as compared to the total score of a FAQLQ-AF administered to said subject at a first time point before being informed is improved by at least 0.5 points, such as at least 1 point, at least 2 points, at least 3 points, or at least 4 points. In some embodiments, the score of a domain of a FAQLQ-AF administered to a subject having a peanut allergy is improved by at least 0.5 points, such as at least 0.5 points in the Allergen Avoidance and Dietary Restrictions domain, at least 0.5 points in the Emotional Impact domain, at least 0.5 points in the Food Allergy Related Health domain, and/or at least 0.5 points in the Risk of Accidental Exposure domain at a second time point after being informed they are to be administered, or are being administered, a peanut composition according to an oral immunotherapy schedule as compared to the score in each domain at a first time point before being informed. In some embodiments, the period of oral immunotherapy between the first time point and the second time point comprises at least one month of therapy. In some embodiments, the period of oral immunotherapy between the first time point and the second time point comprises an up-dosing phase of oral immunotherapy. In some embodiments, the period of oral immunotherapy between the first time point and the second time point is at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a proxy-reported FAQLQ-PF administered to a subject's caregiver. In some embodiments, the total score of a FAQLQ-PF administered to a subject's caregiver at a first time point before an oral immunotherapy or during the up-dosing phase of an oral immunotherapy is 4 or higher. In some embodiments, the score of one or more domains of a FAQLQ-PF administered to a subject's caregiver at a first time point before an oral immunotherapy or during the up-dosing phase of an oral immunotherapy is 4 or higher, such as a score of 4 or higher in the Emotional Impact domain, a score of 4 or higher in the Food-related Anxiety domain, and/or a score of 4 or higher in the Dietary and Social Restrictions domain. In some embodiments, the total score of a FAQLQ-PF administered to a subject's caregiver at a second time point after a period of oral immunotherapy as compared to the total score of a FAQLQ-PF administered to said subject's caregiver at a first time point before the oral immunotherapy is improved by at least 0.5 points, such as at least 1 point, at least 2 points, at least 3 points, or at least 4 points. In some embodiments, the total score of a FAQLQ-PF administered to a subject's caregiver at a second time point after a period of oral immunotherapy as compared to the total score of a FAQLQ-PF administered to said subject's caregiver at a first time point during the up-dosing phase of an oral immunotherapy is improved by at least 0.5 points, such as at least 1 point, at least 2 points, at least 3 points, or at least 4 points. In some embodiments, the score of a domain of a FAQLQ-PF administered to a subject's caregiver is improved by at least 0.5 points, such as at least 0.5 points in the Emotional Impact domain, at least 0.5 points in the Food-related Anxiety domain, and/or at least 0.5 points in the Dietary and Social Restrictions domain at a second time point after a period of oral immunotherapy as compared to the score in each domain at a first time point before the oral immunotherapy or during the up-dosing phase of the oral immunotherapy. In some embodiments, the subject is informed they are to be administered a peanut composition before the oral immunotherapy. In some embodiments, the period of oral immunotherapy between the first time point and the second time point comprises an up-dosing phase of the oral immunotherapy. In some embodiments, the period of oral immunotherapy between the first time point and the second time point is at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a proxy-reported FAQLQ-PF administered to the subject's caregiver. In some embodiments, the total score of a FAQLQ-PF administered to a subject's caregiver at a first time point before the subject is informed they are to be administered, or are being administered, a peanut composition according to an oral immunotherapy schedule is 4 or higher. In some embodiments, the score of one or more domains of a FAQLQ-PF administered to a subject's caregiver at a first time point before the subject is informed they are to be administered, or are being administered, a peanut composition according to an oral immunotherapy schedule is 4 or higher, such as a score of 4 or higher in the Emotional Impact domain, a score of 4 or higher in the Food-related Anxiety domain, and/or a score of 4 or higher in the Dietary and Social Restrictions domain. In some embodiments, the total score of a FAQLQ-PF administered to a subject's caregiver at a second time point after a period after the subject is informed they are to be administered, or are being administered, a peanut composition according to an oral immunotherapy schedule as compared to the total score of a FAQLQ-PF administered to said subject's caregiver at a first time point before the subject is informed is improved by at least 0.5 points, such as at least 1 point, at least 2 points, at least 3 points, or at least 4 points. In some embodiments, the score of a domain of a FAQLQ-PF administered to a subject's caregiver is improved by at least 0.5 points, such as at least 0.5 points in the Emotional Impact domain, at least 0.5 points in the Food-related Anxiety domain, and/or at least 0.5 points in the Dietary and Social Restrictions domain at a second time point after a period after the subject is informed they are to be administered, or are being administered, a peanut composition according to an oral immunotherapy schedule as compared to the score in each domain at a first time point before being informed. In some embodiments, the period of oral immunotherapy between the first time point and the second time point is at least one month of oral immunotherapy. In some embodiments, the period of oral immunotherapy between the first time point and the second time point comprises an up-dosing phase of the oral immunotherapy. In some embodiments, the period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAIM. In some embodiments, the total score of a FAIM administered to a subject having a peanut allergy at a first time point before an oral immunotherapy or during the up-dosing phase of an oral immunotherapy is 4 or higher. In some embodiments, the total score of a FAIM administered to a subject with a peanut allergy after at a second time point after a period of oral immunotherapy as compared to the total score of a FAIM administered to said subject at a first time point before the oral immunotherapy is improved by at least 0.5 points, such as at least 1 point, at least 2 points, at least 3 points, or at least 4 points. In some embodiments, the total score of a FAIM administered to a subject with a peanut allergy at a second time point after a period of oral immunotherapy as compared to the total score of a FAIM administered to said subject at a first time point during the up-dosing phase of an oral immunotherapy is improved by at least 0.5 points, such as at least 1 point, at least 2 points, at least 3 points, or at least 4 points. In some embodiments, the subject is informed they are to be administered a peanut composition before the oral immunotherapy. In some embodiments, the period of oral immunotherapy between the first time point and the second time point comprises an up-dosing phase. In some embodiments, the period of oral immunotherapy between the first time point and the second time point comprises at least 1 month of maintenance therapy, such as at least 2 months, at least 3 months, at least 4 months, at least 5 months, at least 6 months, or at least 12 months of maintenance therapy.

In some embodiments, the quality of life of a subject having a peanut allergy is determined by one or more QoLQs, wherein at least one QoLQ is a FAIM. In some embodiments, the total score of a FAIM administered to a subject having a peanut allergy at a first time point before being informed they are to be administered, or are being administered, a peanut composition according to an oral immunotherapy schedule is 4 or higher. In some embodiments, the total score of a FAIM administered to a subject with a peanut allergy at a second time point after a period after being informed they are to be administered, or are being administered, a peanut composition according to an oral immunotherapy schedule as compared to the total score of a FAIM administered to said subject at a first time point before being informed is improved by at least 0.5 points, such as at least 1 point, at least 2 points, at least 3 points, or at least 4 points. In some embodiments, the period of oral immunotherapy between a first time point and a second time point is at least one month of therapy. In some embodiments, the period between a first time point and a second time point comprises an up-dosing phase of the oral immunotherapy. In some embodiments, the period of oral immunotherapy between a first time point and a second point is at least 1 month of maintenance therapy, such as at least 2 months, at least 3 months, at least 4 months, at least 5 months, at least 6 months, or at least 12 months of maintenance therapy.

Peanut Oral Immunotherapy

In some embodiments, the quality of life of a subject having a peanut allergy can be improved by administering a series of doses of a peanut protein composition, according to a dosing schedule, to the subject during the course of an oral immunotherapy. In some embodiments, the quality of life of a subject having a peanut allergy can be improved by informing the subject they are to be, or are being, administered a series of doses of a peanut protein composition, according to a dosing schedule, to the subject during the course of an oral immunotherapy. In some embodiments, the quality of life of a subject having a peanut allergy can be improved by instructing the subject's caregiver to inform the subject they are to be, or are being, administered a series of doses of a peanut protein composition, according to a dosing schedule, to the subject during the course of an oral immunotherapy.

The full length of the oral immunotherapy, for example the duration of the up-dosing phase, may vary between subjects depending on the age, health conditions, the nature and type of peanut allergy, concurrent interventions, and/or complicating indications, among others. The therapy is generally multi-phasic, and includes at least an up-dosing phase and a maintenance phase. In some embodiments, the oral immunotherapies may further include an initial escalation phase preceding the up-dosing phase. The doses of the peanut protein composition administered in the up-dosing and maintenance phases can be periodically adjusted or scheduled to increase, decrease, or stay the same. The size of the doses of the peanut protein composition administered in the up-dosing and maintenance phases can be adjusted as necessary based on the judgment of a subject's medical caregiver and/or the needs of the subject.

Methods of diagnosing peanut allergy are known in the art and include immunological assays (such as peanut-specific IgE), skin prick tests, food challenges, and trial elimination diets. For diagnosis of peanut allergy by food challenge, the subject receives increasing doses of peanut protein. An observed allergic reaction to the peanut protein during the food challenge indicates the subject has a peanut allergy and is a candidate for peanut oral immunotherapy. The judgment of whether a subject reacts to a particular dose during the food challenge depends on the test criteria, which can vary. A reaction in a food challenge can be judged by the severity of symptoms (e.g., mild, moderate, or severe) and/or the observability of the symptom (e.g., whether a symptom is subjectively reported by the patient or objectively observed by the medical caregiver).

A subject undergoing peanut OIT as described herein for improving the subject's quality of life has a known or suspected peanut allergy. In some embodiments, the subject has previously attempted or completed a peanut protein OIT. In some embodiments, the previous peanut protein OIT was ineffective (for example, by failing to induce acceptable desensitization, producing unacceptable allergic adverse reactions, failing to impart adequate protection from accidental exposure to peanut protein, or failing to improve the subject's quality of life), was terminated by the patient due to discomfort, inconvenience (for example, due to the daily dosing or frequent clinical visits), or necessity (for example, due to reaction to the peanut protein doses and/or due to allergic adverse events during the course of OIT), or was terminated by the patient's medical provider (for example, due to allergic adverse reaction to peanut protein doses and/or due to allergic adverse events during the course of OIT).

A subject undergoing peanut OIT as described herein for improvement of the subject's quality of life may be treatment naïve, having never undergone a peanut OIT for the improvement of their quality of life. A subject being diagnosed for peanut allergy by diagnostic exposure to peanut protein, such as in a food challenge, but with no other history of clinical exposure to peanut protein, is still considered treatment naïve after the diagnostic exposure for the purposes of this application.

The subject receiving the oral immunotherapy treatment for improvement of their quality of life is a human subject. In some embodiments, the subject is about 12 months or older, such as about 12 months to about 48 months (for example, about 12 months to about 24 months, about 24 months to about 36 months, or about 36 months to about 48 months). In some embodiments, the subject is about 4 years or older. In some embodiments, the subject is between 4 years and less than 18 years old. In some embodiments, the subject is 18 years or older.

The up-dosing phase precedes the maintenance phase, and includes administration of a series of escalating doses to reach the maximum dose administered to the subject during the course of oral immunotherapy. The length of time of the up-dosing phase can be adapted according the needs of an individual patient, although is generally completed in about 22 to about 40 weeks. For some patients, the up-dosing phase may last as long as 2 years or more. The up-dosing phase may be extended, for example, if a patient experiences allergic adverse events after beginning a higher dose in the dosing series.

The up-dosing phase of a peanut OIT typically involves incrementally increasing the administered peanut protein dose after a period of time (e.g., approximately every 1-4 weeks). A particular dose in the series is repeatedly (e.g., daily) administered to the patient until advancing to the next dose in the series. In some instances, such as when the subject does not tolerate a particular dose in the series or the subject experiences one or more allergic adverse events, the dose is decreased or the dose in the series is repeated for a period of time prior to advancing to the next dose in the series. The rate of up-dosing (e.g., the length of time an individual dose in the series is administered or the size of the dose increment between doses in the series) may be adjusted based on one or more observed allergic adverse events.

Optionally, the oral immunotherapy includes an initial escalation phase before the up-dosing phase, wherein the subject is administered over the course of one or two days a series of escalating doses. The initial escalation phase is distinguished from the up-dosing phase by a lower dose range, shorter intervals between dose escalations, and, typically, closer monitoring by the subject's medical caregiver. For example, a two day initial escalation may comprise a series of doses from about 0.5 mg to about 6 mg peanut protein, such as individual doses of about 0.5 mg, about 1 mg, about 1.5 mg, about 3 mg, and about 6 mg peanut protein. The highest tolerated dose of the initial escalation phase, or a dose lower than the highest tolerated dose in the initial escalation phase, may be the first dose of the up-dosing phase. If a subject does not tolerate at least a certain dose in the initial escalation phase, the subject may be excluded from the oral immunotherapy. For example, if a subject suffers a serious allergic adverse event after administration of the 0.5 mg, 1 mg, or 1.5 mg peanut protein dose, the subject may not be allowed to proceed to the up-dosing phase. The purposes of the initial escalation phase include calibrating the doses of the up-dosing phase (e.g., the initial dose of the up-dosing phase), and ensuring the suitability of the subject for safely proceeding through an up-dosing phase.

Before, during, or after oral immunotherapy (such as before, during, or after the up-dosing phase, or before, during, or after the maintenance phase), a subject having a peanut allergy, and/or a subject's caregiver, can undergo a quality of life assessment.

Maintenance Phase Dosing Schedules

The maintenance phase of the peanut oral immunotherapy begins after the highest dose of the up-dosing phase is achieved. The maintenance phase is more than about 24 weeks or longer, and may be for the entire life of the patient. For example, the length of the maintenance phase may be more than about 28 weeks, more than about 32 weeks, more than about 36 weeks, more than about 40 weeks, more than about 44 weeks, or more than about 48 weeks. In some embodiments, the maintenance phase is more than about 24 weeks to about 28 weeks, about 28 weeks to about 32 weeks, about 32 weeks to about 36 weeks, about 36 weeks to about 40 weeks, about 40 weeks to about 44 weeks, about 44 weeks to about 48 weeks, about 48 weeks to about 52 weeks, about 52 weeks to about 60 weeks, about 60 weeks to about 72 weeks, about 72 weeks to about 80 weeks, or more than about 80 weeks, such as the life of the subject. In some embodiments, the maintenance phase is up to about 108 weeks in length.

In some embodiments, the maintenance phase dose is administered to the subject daily during at least a portion of the maintenance phase. In some embodiments, the maintenance phase dose is administered to the subject daily for about 6 months to about 2 years during the maintenance phase, such as about 6 months, about 6 months to about 12 months, about 12 months to about 18 months, or about 18 months to about 2 years.

The dosage of peanut protein administered to the subject during the maintenance phase is between about 200 mg and about 1,000 mg peanut protein. For example, in some embodiments, a dose during the maintenance phase is between about 200 mg and about 300 mg peanut protein, about 300 mg and about 500 mg peanut protein, about 500 mg and about 1,000 mg peanut protein, or values and ranges therebetween. In an exemplary embodiment, a maintenance phase dose administered to the subject during the maintenance phase is about 300 mg peanut protein.

Up-Dosing Phase

The up-dosing phase of an oral immunotherapy comprises administering to the patient a series of escalating doses, beginning with a lower dose than the highest dose of the oral immunotherapy and ending with the highest dose of the oral immunotherapy. Each dose in the series of doses is administered periodically, such as daily. Each dose in the series can comprise daily administration of the peanut protein composition for a period of time, such as about 1 week to about 4 weeks, such as about 2 weeks. After the completion of a particular dose in the series for a period of time, treatment can be advanced to a higher dose in the series. In some embodiments, the up-dosing phase of the treatment comprises a series of between 2 and 10 different dose levels. If a subject tolerates a particular dose level during the up-dosing phase for a period of time, the subject can advance to the next dose level in the series of the up-dosing phase. If a subject does not tolerate a particular dose level during the up-dosing phase for a period of time, the subject may repeat the current dose level in the series. Alternatively, if a subject does not tolerate a particular dose level during the up-dosing phase for a period of time, the subject may return to an earlier dose level in the series. The duration of the up-dosing phase therefore depends on the specific responses of the subject. The subject may repeat doses in the series as many times as necessary to achieve the highest dose in the series. The up-dosing phase ends when the highest dose is tolerated for two weeks.

The pharmaceutical composition of peanut protein of a dose administered during the up-dosing phase comprises between about 0.5 mg and about 5,000 mg of peanut protein, such as about 0.5 mg to about 10 mg peanut protein, about 10 mg to about 100 mg peanut protein, about 100 mg to about 300 mg peanut protein, about 300 mg to about 500 mg peanut protein, about 500 mg to about 1,000 mg peanut protein, about 1,000 mg to about 2,000 mg peanut protein, or about 2,000 mg to about 5,000 mg peanut protein and values and ranges therebetween. In a non-limiting exemplary embodiment, the doses of the up-dosing phase are daily administrations of the maximum tolerated dose of the initial escalation phase, such as 3 mg or 6 mg peanut protein, followed by a series of doses of about 12 mg peanut protein, about 20 mg peanut protein, about 40 mg peanut protein, about 80 mg peanut protein, about 120 mg peanut protein, about 160 mg peanut protein, about 200 mg peanut protein, about 240 mg peanut protein, and about 300 mg peanut protein, wherein each dosage level is administered for about 1 week to about 4 weeks (such as about 2 weeks) before advancing to the next dose in the series. In another exemplary embodiment, the doses of the up-dosing phase are daily administrations of the maximum tolerated dose of the initial escalation phase, such as 3 mg or 6 mg peanut protein, followed by a series of escalating daily doses prescribed by a subject's medical caregiver, wherein each daily dose comprises one or more capsules or sachets selected from the group consisting of: 0.5 mg peanut protein capsules, 1 mg peanut protein capsules, 10 mg peanut protein capsules, 20 mg peanut protein capsules, 100 mg peanut protein capsules, or 300 mg peanut protein sachets, wherein each dosage level is administered for about 1 week to about 4 weeks (such as about 2 weeks) before advancing to the next dose in the series.

The series of doses of the up-dosing phase are distinguished by adjustment of the administered dose. The size of the dose in the series of doses of the up-dosing phase are adjusted periodically, such as between once every week and once every six weeks. In some embodiments, the up-dosing phase comprises weekly dose adjustment, dose adjustment every two weeks, dose adjustment every third week, dose adjust every fourth week, dose adjustment every fifth week, dose adjustment every sixth week, or adjustment as needed based on the judgment of the subject's medical caregiver. The dose may be increased to the next scheduled dose in the series, lowered to a previous in the series in response to an allergic adverse event, maintained for an additional interval at the current dose in the series, increased to a higher dose in the series based on the judgment of the subject's medical caregiver, or decreased to a lower dose in the series based on the judgment of the subject's medical caregiver. In some embodiments, the up-dosing phase is adjusted at any time based on the judgment of the subject's medical caregiver that the subject did not tolerate the current dose in the series.

The up-dosing phase proceeds until the subject achieves the final dose in the up-dosing series. In some embodiments, the up-dosing phase is about 1 month to about 6 months, such as about 1 month to about 3 months, or about 3 months to about 6 months. In some embodiments, the up-dosing phase is about 6 months to about 2 years, such as about 6 months to about 1 year, about 1 year to about 18 months, or about 18 months to about 2 years. In a non-limiting exemplary embodiment, the up-dosing phase continues for 22 weeks to 2 years, depending on the number of dose reductions and re-escalations and dose level repeats, through doses of 12 mg peanut protein, 20 mg peanut protein, 40 mg peanut protein, 80 mg peanut protein, 120 mg peanut protein, 160 mg peanut protein, 200 mg peanut protein, 240 mg peanut protein, and terminating at 300 mg peanut protein. In any of the described embodiments, the up-dosing phase terminates when the subject tolerates the scheduled dose of the final dose in the series of the up-dosing phase for 2 weeks, thereby beginning the maintenance phase.

Each dose of the series of the up-dosing phase may be scheduled to last about 1 week, about 2 weeks, about 3 weeks, about 4 weeks, or values and ranges therebetween. Based on the observation of an allergic adverse event, a subject's caregiver may repeat the subject's current dose in up-dosing series. A particular portion with a particular dose may be repeated as many times as necessary, such as once, two times, three times, or four times, or more, to adequately desensitize a subject to that dose, such as when the subject no longer experiences a moderate or serious allergic adverse event upon accidental (or deliberate) exposure to the food allergen.

Initial Escalation Phase

Optionally, the oral immunotherapy includes an initial escalation phase preceding the up-dosing phase. The initial escalation phase can ensure the safety and suitability of oral immunotherapy for a particular subject. The initial escalation phase is administered over a short period, such as one or two days, at an appropriate medical facility, such as a doctor's office or allergy clinic. The subject is usually closely monitored by a medical caregiver, who can provide interventions such as epinephrine, albuterol, and diphenhydramine in the event of an allergic adverse reaction that necessitates intervention. The initial escalation phase of the oral immunotherapy, if present, includes administration of a plurality of small doses of the peanut protein composition to the subject. The small doses can be spaced by a period of time, such as about 10 minutes to about 60 minutes, and can include 1, 2, 3, 4, or 5 or more doses.

The initial escalation phase may comprise doses between about 0.5 mg and about 6 mg peanut protein, such as about 0.5 mg to about 1.5 mg peanut protein, about 1.5 mg to about 3 mg peanut protein, or about 3 mg to about 6 mg peanut protein. In a non-limiting example, the initial escalation phase comprises an incremental escalation over one day from about 0.5 mg peanut protein to a maximum of about 6 mg peanut protein in a single day, with single doses of about 0.5 mg, about 1 mg, about 1.5 mg, about 3 mg, and about 6 mg of peanut protein, wherein tolerance of the 3 mg or 6 mg peanut protein dose indicates the subject can safely proceed to an up-dosing phase of an oral immunotherapy.

Compositions for Oral Immunotherapy

Exemplary compositions for treating peanut allergy are described in detail in U.S. Publication No. 2014/0271721, the contents of which are incorporated by reference herein in its entirety. Exemplary methods for preparing peanut protein formulations are described in detail in U.S. Publication No. 2014/0271836, the contents of which are incorporated by reference herein in its entirety.

The quality of life of a subject having a peanut allergy can be improved by administering a series of doses of a peanut protein composition to the subject during the course of a peanut protein oral immunotherapy. The peanut protein composition is preferably a pharmaceutical composition comprising one or more peanut allergen proteins for treating peanut allergy. In some embodiments, peanut proteins may be isolated from peanut flour and, optionally, further comprise one or more diluents, one or more glidants, and one or more lubricants. In some embodiments, the pharmaceutical composition of peanut protein comprises between about 0.05% to about 100% w/w of peanut protein.

In some embodiments, the pharmaceutical composition of peanut protein comprises characterized peanut protein. In some embodiments the characterized peanut protein comprises characterized peanut allergen proteins Ara h1, Ara h2, and/or Ara h6. In one embodiment, a final formulation for treating peanut allergy comprises peanut flour, comprising characterized peanut allergen proteins Ara h1, Ara h2, and/or Ara h6, formulated with a diluent, a glidant, and a lubricant in graduated doses comprising capsules containing between about 0.5 and about 5,000 mg of peanut protein for administration in up-dosing, maintenance, and/or initial escalation phases of an oral immunotherapy.

In any of the methods described herein, the pharmaceutical composition of peanut protein for administration in a maintenance phase of an oral immunotherapy may comprise a dose of between about 200 mg to about 1,000 mg peanut protein, such as between about 200 mg and about 250 mg peanut protein, about 250 mg and about 300 mg peanut protein, about 300 mg and about 500 mg peanut protein, and about 500 mg and about 1,000 mg peanut protein. In a non-limiting preferred embodiment, the dose of peanut protein for administration in the maintenance phase of an oral immunotherapy is about 300 mg peanut protein.

In some embodiments, the pharmaceutical composition of peanut protein for administration in an up-dosing phase of an oral immunotherapy comprises between about 0.5 mg and about 5,000 mg peanut protein, such as individual doses in a series of about 3 mg, about 6 mg, about 10 mg, about 12 mg, about 20 mg, about 40 mg, about 80 mg, about 100 mg, about 120 mg, about 160 mg, about 200 mg, about 240 mg, and about 300 mg peanut protein. In a non-limiting exemplary embodiment, the doses of peanut protein for administration in an up-dosing phase of an oral immunotherapy are daily administration of the maximum tolerated dose of the initial escalation phase, such as about 3 mg peanut protein or about 6 mg peanut protein, followed by a series of escalating daily doses prescribed by a subject's medical caregiver, wherein each daily dose comprises one or more capsules or sachets selected from the group consisting of: about 0.5 mg peanut protein capsules, about 1 mg peanut protein capsules, about 10 mg peanut protein capsules, about 20 mg peanut protein capsules, about 100 mg peanut protein capsules, or about 300 mg peanut protein sachets, wherein each dosage level is administered for about 1 week to about 4 weeks (such as about 2 weeks) before advancing to the next dose.

In the methods described herein, an oral immunotherapy may optionally comprise an initial escalation phase. In some embodiments, the pharmaceutical composition of peanut protein for administration in an initial escalation phase of an oral immunotherapy comprises between about 0.5 and about 6 mg of peanut protein, such as individual doses of about 0.5 mg, about 1 mg, about 1.5 mg, about 3 mg, and about 6 mg peanut protein. In some embodiments, the pharmaceutical composition of peanut protein for administration in an initial escalation phase of an oral immunotherapy comprises between about 0.5 and about 6 mg of peanut protein, such as individual doses of about 0.5 mg, about 1 mg, about 1.5 mg, about 3 mg, about 6 mg, and about 12 mg peanut protein.

EXEMPLARY EMBODIMENTS

The invention may be better understood by reference to the following exemplary embodiments. However, the exemplary embodiments are not intended to limit the scope of the invention described herein.

Embodiment 1. A method of improving the quality of life of a patient with a peanut allergy, comprising: administering to the patient a peanut composition according to an oral immunotherapy schedule.

Embodiment 2. The method of embodiment 1, wherein the patient is informed that the peanut composition is being administered.

Embodiment 3. The method of embodiment 2, wherein the patient is informed that the peanut composition is being administered to the patient at the start of the oral immunotherapy schedule.

Embodiment 4. The method of embodiment 2, wherein the patient is informed that the peanut composition is being administered to the patient during an up-dosing phase of the oral immunotherapy schedule.

Embodiment 5. The method of embodiment 2, wherein the patient is informed that the peanut composition is being administered to the patient during a maintenance phase of the oral immunotherapy schedule.

Embodiment 6. The method of embodiment 1, further comprising informing the patient that the peanut composition is being administered to the patient.

Embodiment 7. The method of embodiment 6, wherein the patient is informed that the peanut composition is being administered to the patient prior to the start of the oral immunotherapy schedule.

Embodiment 8. The method of embodiment 6, wherein the patient is informed that the peanut composition is being administered to the patient during an up-dosing phase of an oral immunotherapy schedule.

Embodiment 9. The method of embodiment 6, wherein the patient is informed that the peanut composition is being administered to the patient during a maintenance phase of the oral immunotherapy schedule.

Embodiment 10. The method of any one of embodiments 1-9, wherein the quality of life improvement is measured using a quality of life questionnaire (QoLQ).

Embodiment 11. The method of embodiment 10, wherein the QoLQ comprises one or more scored domains of measurement.

Embodiment 12. The method of embodiment 11, wherein the QoLQ is a Food Allergy Quality of Life Questionnaire (FAQLQ).

Embodiment 13. The method of embodiment 12, wherein the FAQLQ is a FAQLQ-child form (FAQLQ-CF), FAQLQ-teen form (FAQLQ-TF), FAQLQ-adult form (FAQLQ-AF), or FAQLQ-parent form (FAQLQ-PF).

Embodiment 14. The method of embodiment 10, wherein the QoLQ is a Food Allergy Independent Measure (FAIM).

Embodiment 15. The method of embodiment 14, wherein the FAIM is a FAIM-child form (FAIM-CF), FAIM-teen form (FAIM-TF), FAIM-adult form (FAIM-AF), or FAIM-parent form (FAIM-PF).

Embodiment 16. A method of improving the quality of life of a patient with a peanut allergy, as assessed by a quality of life questionnaire (QoLQ), the method comprising administering to the patient a peanut composition according to an oral immunotherapy schedule.

Embodiment 17. The method of embodiment 16, wherein the patient is informed that the peanut composition is being administered.

Embodiment 18. The method of embodiment 17, wherein the patient is informed that the peanut composition is being administered to the patient at the start of the oral immunotherapy schedule.

Embodiment 19. The method of embodiment 17, wherein the patient is informed that the peanut composition is being administered to the patient during an up-dosing phase of the oral immunotherapy schedule.

Embodiment 20. The method of embodiment 17, wherein the patient is informed that the peanut composition is being administered to the patient during a maintenance phase of the oral immunotherapy schedule.

Embodiment 21. The method of embodiment 16, further comprising informing the patient that the peanut composition is being administered to the patient.

Embodiment 22. The method of embodiment 21, wherein the patient is informed that the peanut composition is being administered to the patient prior to the start of the oral immunotherapy schedule.

Embodiment 23. The method of embodiment 21, wherein the patient is informed that the peanut composition is being administered to the patient during an up-dosing phase of an oral immunotherapy schedule.

Embodiment 24. The method of embodiment 21, wherein the patient is informed that the peanut composition is being administered to the patient during a maintenance phase of the oral immunotherapy schedule.

Embodiment 25. The method of any one of embodiments 16-24, wherein the QoLQ comprises one or more scored domains of measurement.

Embodiment 26. The method of embodiment 25, wherein the QoLQ is a Food Allergy Quality of Life Questionnaire (FAQLQ).

Embodiment 27. The method of embodiment 26, wherein the FAQLQ is a FAQLQ-child form (FAQLQ-CF), FAQLQ-teen form (FAQLQ-TF), FAQLQ-adult form (FAQLQ-AF), or FAQLQ-parent form (FAQLQ-PF).

Embodiment 28. The method of embodiment 25, wherein the QoLQ is a Food Allergy Independent Measure (FAIM).

Embodiment 29. The method of embodiment 28, wherein the FAIM is a FAIM-child form (FAIM-CF), FAIM-teen form (FAIM-TF), FAIM-adult form (FAIM-AF), or FAIM-parent form (FAIM-PF).

Embodiment 30. The method of embodiment 25, wherein the QoLQ is a Pediatric Quality of Life Inventory (PedsQL).

Embodiment 31. The method of any one of embodiments 1-30, wherein the quality of life is improved for at least 6 months.

Embodiment 32. The method of any one of embodiments 1-31, wherein the quality of life is improved for at least 12 months.

Embodiment 33. The method of any one of embodiments 11-13 or 25-27, wherein the one or more scored domains of the QoLQ are each scored on a scale between 1 and 7, or are each converted to a score between a first score and a second score, wherein the second score indicates worse quality of life.

Embodiment 34. The method of any one of embodiments 11-13 or 25-27, wherein an improvement in the patient's quality of life is at least 0.5 points in one or more domains of the QoLQ at a second time point after a period of oral immunotherapy as compared to an assessment at a first time point before the period of oral immunotherapy.

Embodiment 35. The method of any one of embodiments 11-17 or 25-34, wherein an improvement in the patient's quality of life is at least 0.5 points in a total score of the QoLQ at a second time point after a period of oral immunotherapy as compared to an assessment at a first time point before the period of oral immunotherapy; wherein the total score is the average of each domain score.

Embodiment 36. The method of embodiment 34 or embodiment 35, wherein the period of oral immunotherapy between the first time point and the second time point is the up-dosing phase of the oral immunotherapy schedule.

Embodiment 37. The method of embodiment 34 or embodiment 35, wherein the period of oral immunotherapy between the first time point and the second time point is at least 1 month of a maintenance therapy of the oral immunotherapy schedule.

Embodiment 38. The method of any one of embodiments 1-37, wherein the quality of life improves after 6 months of the oral immunotherapy schedule.

Embodiment 39. The method of any one of embodiments 1-38, wherein the oral immunotherapy schedule comprises an up-dosing phase and a maintenance phase.

Embodiment 40. The method of embodiment 39, wherein the peanut composition is administered to the patient during the maintenance phase on a daily basis.

Embodiment 41. The method of embodiment 39 or embodiment 40, wherein the maintenance phase is at least 3 months.

Embodiment 42. The method of any one of embodiments 39-41, wherein the peanut composition is administered to the patient during a maintenance phase of the oral immunotherapy schedule at a dose of about 300 mg peanut protein or more.

Embodiment 43. The method of any one of embodiments 39-42, wherein the up-dosing phase comprises administering to the patient two or more different doses between about 3 mg and about the dose of an initial maintenance phase dose.

Embodiment 44. The method of any one of embodiments 1-43, wherein the oral immunotherapy schedule comprises an up-dosing phase that is between about 3 months and about 2 years in length.

Embodiment 45. The method of any one of embodiments 1-44, wherein the oral immunotherapy schedule further comprises an initial escalation phase.

Embodiment 46. The method of any one of embodiments 1-45, wherein the patient is about 4 years old or older.

Embodiment 47. The method of any one of embodiments 1-46, wherein the patient is between about 4 years old and about 17 years old.

Embodiment 48. The method of any one of embodiments 1-47, wherein the patient is between about 8 years old and about 17 years old.

Embodiment 49. The method of any one of embodiments 1-48, wherein the method comprises measuring the quality of life before administering to the patient a peanut composition according to an oral immunotherapy schedule.

Embodiment 50. The method of any one of embodiments 1-49, wherein the method comprises measuring the quality of life after administering to the patient a peanut composition according to an oral immunotherapy schedule.

Embodiment 51. The method of any one of embodiments 2-15 or 17-50, wherein the method comprises measuring the quality of life after informing the patient that the peanut composition is being administered.

Embodiment 52. The method of any one of embodiments 1-51, wherein the quality of life of the patient is improved as determined by a quality of life questionnaire (QoLQ).

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods described herein.

Example 1—Impact of Peanut Allergy on Quality of life

A study was undertaken to assess the real-world burden of peanut allergy on patients and caregivers in the United States.

In one portion of the study, adolescents 13-17-years-old and caregivers of adolescents 13-17-years-old with self-reported, provider-diagnosed peanut allergy completed a validated, age-appropriate Food Allergy Quality of Life Questionnaire (FAQLQ-TF for self-report or a FAQLQ-PF for proxy-report; wherein for each answer 1=no issue and 7=extreme issue). Between-group analyses were conducted (chi square; t-tests). The adolescents (n=102) and the caregivers for adolescents (n=94) completed the survey. Key demographic and disease history variables among adolescents (self-report versus proxy-report) were similar. Adolescents reported significantly greater burden, versus caregivers, regarding limitations that living with peanut allergy placed on their day-to-day life and fear of a reaction impacting emotional well-being, and greater care in avoiding direct contact with peanuts. Adolescents had higher scores (i.e., poorer quality of life) on the FAQLQ Emotional scale compared with caregiver assessment (mean 5.07 versus 4.21, p<0.001). Adolescents and caregivers also differed significantly on the most concerning aspects of PA, with adolescents expressing more concern regarding physical symptoms during a reaction and the impact of peanut allergy on the family, compared with caregivers of adolescents. In total, adolescents reported poorer quality of life (impact on day-to-day life, emotional well-being, and FAQLQ emotional scale), greater concern regarding physical symptoms of reaction and impact on family, and greater care in avoiding exposure to peanuts than did caregivers.

Of the self-reported adolescents who completed the FAQLQ-TF, a number of variables were statistically significant correlates of FAQLQ-TF Total score: psychosocial variables, including impact of fear of a reaction on emotional well-being (p<0.001), daily life limitations (p<0.001), worry regarding epinephrine autoinjector access (p<0.001), confidence managing a reaction (p=0.025), total number of uses of advanced interventions (ER, hospital, IV epinephrine, or intubation) in their lifetime (p=0.003), and severity of their most severe reaction (p=0.006). There were no statistically significant correlations with age, sex, number of other food allergies, and other health conditions, time since most recent reaction and since the most severe reaction, the lifetime number of moderate/severe reactions, and the number of reactions in the last year. These data suggest that psychosocial variables and the need to modify daily activities to practice avoidance, and a history of needing to seek advanced treatment due to exposure, are associated with a decreased disease-specific quality of life.

In another portion of the study, adolescents 13-17-years-old with self-reported, provider-diagnosed peanut allergy completed the Pediatric Quality of Life Inventory (PedsQL; scores 0-100, higher is better quality of life). Between-group analyses were conducted (chi square; t-test). The adolescents with peanut allergy (n=102) had a mean PedsQL Total score of 48.8. Mean subscale scores were: Physical (53.6), Emotional (43.0), Social (48.2), School (46.0), and Psychosocial (44.5). These scores were significantly below the scale scores from a general population of 8-16-year-olds (n>5900; range 78.2-87.0) and exceeded the minimum clinically important difference (4.36-9.12 points). Adolescents experienced ≥1 peanut allergy-related reaction in the past year had significantly lower PedsQL Total score (p=0.008), as did those receiving clinician intervention for >1 peanut allergy reaction in the past year (p<0.001, those "not at all" to "somewhat satisfied" with current approaches to peanut allergy reaction prevention (p=0.012), those saying peanut allergy limited their day-to-day life "somewhat" to "completely" (p=0.013), or who reported a "great" to "100% chance" of not effectively dealing with a reaction. Thus, adolescents with peanut allergy have substantially lower PedsQL scores than the general population of similarly aged individuals. PedsQL Total scores were significantly different between subgroups defined by recent allergic reaction/need for clinician intervention, satisfaction with reaction prevention, perceived limitations on day-to-day life, and concern about their ability to deal with a reaction.

Example 2—Peanut Oral Immunotherapy Clinical Trials

A) Double-blind clinical trial. A randomized, double-blind, placebo-controlled Phase 3 clinical trial (PALISADE) was conducted with peanut-allergic subjects aged 4 to 49 years old. Subjects underwent an initial escalation, followed by an up-dosing phase to a target dose of 300 mg per day of peanut protein, followed by an approximately six-month maintenance phase comprising administration of 300 mg per day of peanut protein. See Jones et al., *Efficacy and Safety of AR101 in Peanut Allergy: Results from a Phase 3, Randomized, Double-Blind, Placebo-Controlled Trial (PALISADE)*, J. Allergy Clin. Immunol. 141(2), suppl. AB400 (2018); and Vickery et al., AR101 *Oral Immunotherapy for Peanut Allergy*, New England J. Medicine, vol. 379, no. 21, pp. 1991-2001 (2018).

At baseline screening and at exit of PALISADE, subjects (self-report) and their parents or guardians/caregivers (proxy-report) completed an age-appropriate Food Allergy Quality of Life Questionnaire (FAQLQ; e.g., FAQLQ-CF, FAQLQ-TF, or FAQLQ-PF). Domain and total scores for subjects aged ≥8 and parents/caregivers of subjects 4-17-years-old were calculated. To report results across the clinical trial, self-report FAQLQ scores were combined into a single child, teen, and adult form (termed FAQLQ-CTAF) using common items (i.e., questions). The scale range was 1-6 or 1-7, with a higher score indicating a worse QoL. Relationships to demographic and disease history variables were also evaluated. 367 peanut-allergic subjects and 442 parents/caregivers completed baseline assessments. Results indicated peanut allergy had a significant impact on subject quality of life. For self-reporting, Emotional Impact had the highest score (4.80), followed by Allergen Avoidance and Dietary Restrictions (4.40), and Risk of Accidental Exposure (4.20). For parents/caregivers, Food Anxiety had the highest score (4.23), followed by Social and Dietary Limitations (4.17) and Emotional Impact (3.82). See Wang et al., *Impact of Peanut Allergy on Quality of Life: Baseline Results from PALISADE, a Phase 3, Double-Blind, Placebo-Controlled Trial for AR101 Oral Immunotherapy*, J. Allergy Clin. Immunol. 143(2) (2019).

At baseline screening and at exit of PALISADE, subjects (self-report) and their parents or guardians (proxy-report) also completed an age-appropriate Food Allergy Independent Measure (FAIM; e.g., FAIM-CF or FAIM-PF). The FAIM questionnaires consist of expectation-of-outcome and disease severity questions. Each FAIM question was scored from 1 to 7, with a higher score indicating a worse QoL (e.g., greatest severity perception or worse expectation of outcome).

B) Open label extension. Some PALISADE completers that were treated with an active formulation (i.e., non-placebo) elected to participate in an open-label extension (OLE) follow-on clinical trial, wherein the subject was informed that they would continue receiving active treatment. Prior to beginning the OLE (at PALISADE exit), subjects (self-report) and/or their parents or caregivers/guardians (proxy-report) completed an age-appropriate FAQLQ (e.g., FAQLQ-CF, FAQLQ-TF, or FAQLQ-PF) or FAIM (e.g., FAIM-CF or FAIM-PF). As above, to report results across the trial, self-reported FAQLQ scores were combined using common items. Subjects participating in the OLE received approximately 6 additional months (i.e., approximately 28 weeks) of maintenance therapy comprising daily administrations of 300 mg of peanut protein. At the end of the approximately 6 additional months of OLE maintenance therapy (i.e., after approximately 52 weeks total of 300 mg daily peanut protein maintenance therapy), subjects received an exit double-blind placebo-controlled food challenge (DBPCFC). Subjects and/or their parents/caregivers completed an exit age-appropriate FAQLQ (e.g., FAQLQ-CF, FAQLQ-TF, or FAQLQ-PF) and FAIM (e.g., FAIM-CF or FAIM-PF).

C) Results. 110 peanut-allergic subjects entered the OLE and 103 completed the additional 6 months of daily maintenance therapy. Of those enrolling in the OLE trial, 62.7% were between 4 and 11 years old, and the remaining 37.2% were between 12 and 17 years old.

Among the 68 patients between 8 and 17-years-old who completed the FAQLQ self-assessment at the end of the OLE, statistically significant improvements above the developer-reported minimum clinically important difference (MCID) were seen on all individual scales (Allergy Avoidance and Dietary Restrictions, Risk of Accidental Exposure, and Emotional Impact) and the Total Score (all $p<0.01$) compared to the FAQLQ PALISADE baseline assessments, as reported in FIG. 1. Among the 72 patients between 8 and 17-years-old who completed the FAIM self-assessment at the end of the OLE, statistically significant improvements above the developer-reported MCID were seen on the Expectation of Outcomes questions and the total score. Decreases below the MCID were observed for the questions of Product Avoidance and Social Impact. Subjects reported improvements in QoL both from PALISADE screening to PALISADE exit (a blinded period) and from PALISADE exit to the OLE exit (an open-label period). For the FAQLQ self-reports, these changes were of similar magnitude.

Figure 2:
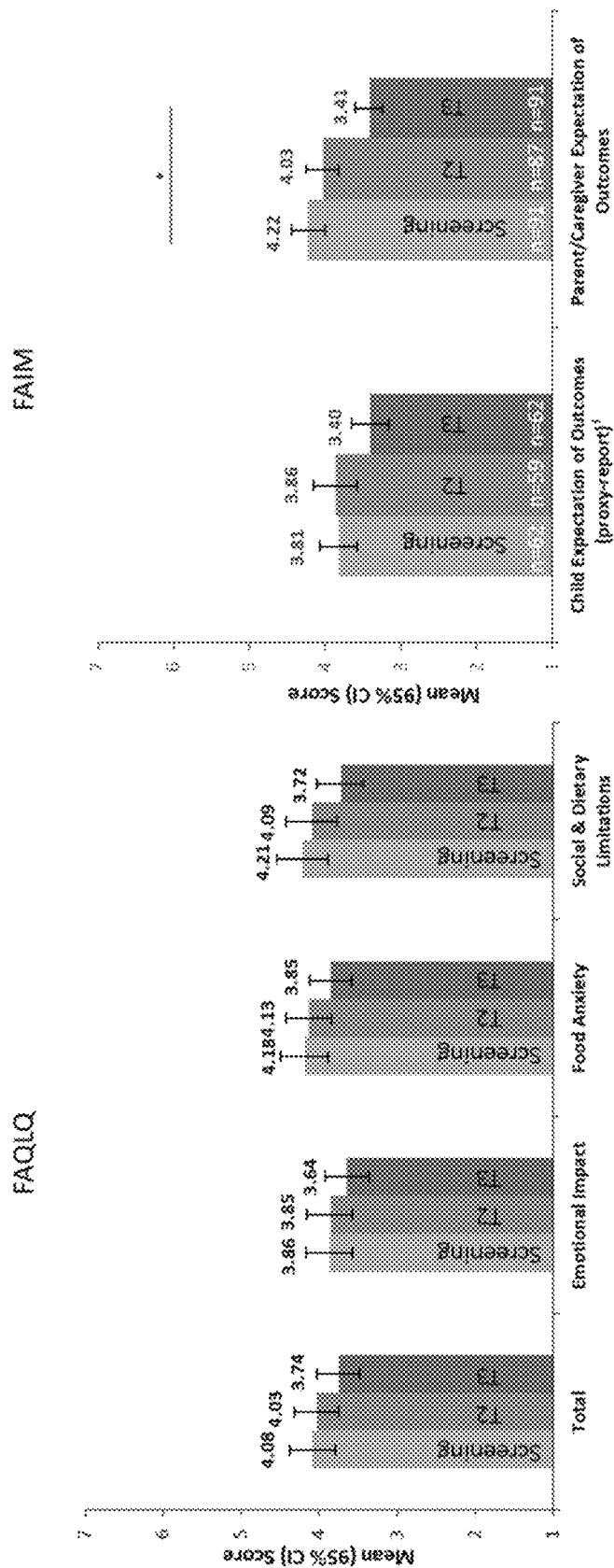
FIG. 2 shows proxy-reported quality of life results regarding subjects (ages 4-17 years) participating in two peanut OIT clinical trials (PALISADE and an open label extension of PALISADE) as measured by a Food Allergy Quality of Life Questionnaire (FAQLQ; e.g., FAQLQ-PF) and by a Food Allergy Independent Measure (FAIM; e.g., FAIM-PF) at three time points (left: FAQLQ; right: FAIM). The first time point occurred during the screening of the first clinical trial (PALISADE). The second time point (T2) occurred after the completion of a double-blind placebo controlled food challenge (DBPCFC) administered at PALISADE exit and before the start of the open label extension. The third time point (T3) occurred at the exit of the open label extension. The left panel of FIG. 2 shows mean scores (with 95% confidence interval indicated) for the FAQLQ total score and for domains of Emotional Impact, Food Anxiety, and Social & Dietary Limitations. The right panel of FIG. 2 shows mean scores (with 95% confidence interval indicated) for the FAIM Child Expectation of Outcomes (by proxy) and Parent/Caregiver Expectation of Outcomes. For the Child Expectation of Outcomes (by proxy), parents or caregivers of children age 13-17 were not tested for this question. The Parent/Caregiver Expectation of Outcomes question exceeded the minimum clinically important difference (MCID) between PALISADE screening and T3, and is indicated by an asterisk above the bars.

As reported in FIG. 2, statistically significant improvements were also observed for two of the three domains of the FAQLQ-PF completed by parents/guardians regarding 93 peanut-allergic subjects participating in the OLE (Social and Dietary Limitations: $p<0.01$; Food Anxiety: $p<0.05$; Emotional Impact: $p=0.07$) and the Total Score was also significant ($p<0.01$) compared to baseline FAQLQ-PF baseline assessments. None of the proxy-reported FAQLQ scores exceeded the threshold indicating a MID as reported by the developer, however. For the FAIM questionnaire, the Child Expectation of Outcomes (by proxy) was only collected from parents/caregivers of children below 13-years-old. Of these 62 parents/caregivers of peanut-allergic children who completed the OLE, a statistically significant decrease in the Child Expectation of Outcomes (by proxy) domain was observed, although the decrease did not exceed the developer-reported MCID. Of the 91 parents/caregivers of peanut-allergic children who completed the OLE, the Parent/Caregiver Expectation of Outcomes domain indicated a statistically significant reduction in domain score at the end of the OLE. This decrease exceeded the developer-reported MID. In contrast to the self-reported QoL measures, the majority of the improvement in QoL as reported by proxy was after the peanut-allergic subjects had been informed they were receiving the peanut protein composition, i.e., after the open label period.

Figure 3:
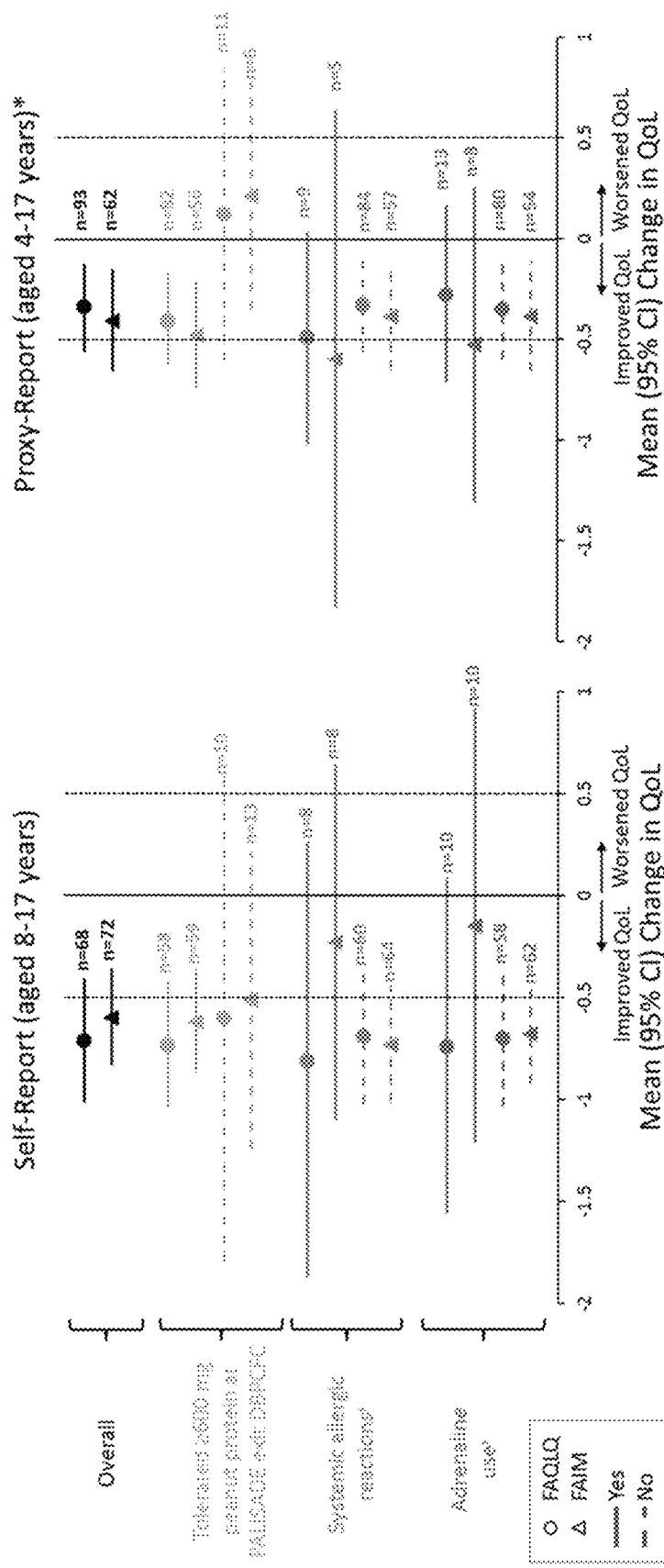
FIG. 3 shows the change in quality of life of various subjects from the screening of a first peanut OIT clinical trial (PALISADE) to the exit of the open label extension of PALISADE, including a time point between PALISADE and the open label extension. Circular points indicate mean (with 95% confidence interval indicated) change in the Food Allergy Quality of Life Questionnaire (FAQLQ) total scores either by self-report (e.g., FAQLQ-CF or FAQLQ-TF) or by proxy-report (e.g., FAQLQ-PF). Triangular points indicate mean (with 95% confidence interval indicated) change in Food Allergy Independent Measure (FAIM) total scores either by self-report (e.g., FAIM-CF or FAIM-TF) or by proxy-report (e.g., FAIM-PF). Solid and dashed lines indicate "yes" and "no," respectively, with respect to whether the particular subjects tolerated at least 600 mg peanut protein at a time point in-between the two clinical trials (i.e., the PALISADE exit) as measured in a double-blind placebo-controlled food challenge, whether the subjects experienced systemic allergic reactions during either the first clinical trial (PALISADE) or the open label extension, and whether subjects reported using adrenaline during the first clinical trial (PALISADE) or the open label extension. The dashed vertical line (+/−0.5 score change) indicates the minimum clinically important difference (MCID) per the QoL instrument.

These FAQLQ and FAIM data were also analyzed by variable of food challenge outcome, adverse events, and adrenaline use. As indicated in FIG. 3, subjects who completed the OLE were divided based on tolerating the 600 mg peanut protein dose in the OLE exit double-blind placebo-controlled food challenge, on the occurrence of a systemic allergic reaction during either of PALISADE or the OLE clinical trial, and the use of adrenaline during either of PALISADE or the OLE clinical trial. In FIG. 3, the proxy-report for FAIM is limited to Child Expectation of Outcomes score for subjects aged 4-12-years-old. Peanut protein OIT was consistently correlated with improvement in self-assessed QoL. The efficacy of the OIT (as measured by the oral food challenge, the presence of systemic allergic reactions, and the use of adrenaline) was associated with reduced improvement, but still improved as compared to baseline. Surprisingly, improvements in proxy-reported QoL were consistently less substantial than the self-assessments, suggesting parents/caregivers underestimated the improvement in their children's QoL. The difference in proxy-reported QoL by parents/caregivers of children who did not tolerate the 600 mg peanut protein dose in the oral food challenge as compared to children who did tolerate the 600 mg peanut protein dose was also more pronounced than the self-assessments.

D) Additional treatment cohort. In addition to the cohort of patients described above (termed "cohort 1" of the open label extension), another cohort of patients entered the open label extension (termed "cohort 3a"). Subjects in cohort 3a, like cohort 1 subjects, were PALISADE completers that had been treated with an active formulation (i.e., non-placebo) and elected to participate in the open-label extension follow-on clinical trial, wherein they were informed that they would continue receiving active treatment. Prior to beginning the OLE (at PALISADE exit), cohort 3a subjects (self-report) and/or their parents or caregivers/guardians (proxy-report) completed an age-appropriate FAQLQ or FAIM, as with the cohort 1 subjects described above. Subjects in cohort 3a received approximately 56 additional weeks of maintenance therapy comprising daily administrations of 300 mg of peanut protein. At the end of the approximately 56 additional weeks of maintenance therapy (i.e., after approximately 82 weeks total of 300 mg daily peanut protein maintenance therapy), subjects received an exit double-blind placebo-controlled food challenge. Cohort 3a subjects and/or their parents/caregivers completed an exit age-appropriate FAQLQ and FAIM.

31 subjects were assigned to cohort 3a, of which 16 completed the exit FAQLQ and 17 completed the exit FAIM assessment. As in cohort 1, cohort 3a subject's FAQLQ scores exceeded the developer-reported MID of −0.5 for Total scores (mean change −0.63, range −1.36, 0.11). In cohort 1, all subdomains exceeded the MID, whereas in cohort 3a only Emotional Impact improved beyond the MID. For both cohorts, FAIM Total scores exceeded the MID (for cohort 1, n=72, mean change −0.60, range −0.83 to −0.36; for cohort 3a, n=17, mean change −0.83, range −1.39 to −0.37). For the FAIM, only subject Expectation of Outcome score exceeded the MID, whereas for cohort 3a subjects all subdomain FAIM scores improved beyond the MID. These results indicate that the overall improvement in quality of life after subjects are informed they are on active therapy is maintained over a longer maintenance therapy.

Together, these results suggest peanut OIT may substantially improve patient-reported QoL across domains of measurement. These improvements may exceed patient's parent/caregiver expectations. Improvements occurred between initial screening and the initial exit measurement, where the initial exit measures were taken immediately after unblinding of the first trial and after initial desensitization and a maintenance period. However, even though significant desensitization was achieved during the blinded trial, quality of life improvements continued to manifest during the unblinded open-label extension trial, leading to even more substantial improvements across the population.

Example 3—European Peanut Oral Immunotherapy Clinical Trial

A) Trial design. A European phase 3 trial (ARTEMIS) was conducted with peanut-allergic children who experienced dose-limiting symptoms at ≤300 mg peanut protein (~1 peanut kernel) during an entry double-blind placebo-controlled food challenge (DBPCFC). The trial was a randomized, placebo-controlled, multicenter trial conducted at 18 sites in seven European countries: Ireland, France, Germany, Italy, Spain, Sweden, and the United Kingdom.

Children aged 4-17 years were eligible for enrollment if they had a clinical history of peanut allergy, had a mean peanut skin prick test (SPT) wheal diameter ≥3 mm compared to negative control and/or a serum peanut-specific immunoglobulin E (psIgE) level ≥0.35 $kU_A/L$ (as determined by ImmunoCAP®) and experienced dose-limiting symptoms at ≤300 mg peanut protein during an entry DBPCFC. Major exclusion criteria included any severe or life-threatening episode of anaphylaxis within 60 days of the screening DBPCFC, severe or uncontrolled asthma, a history of eosinophilic esophagitis, or chronic, recurrent, or severe gastrointestinal (GI) symptoms of undiagnosed etiology.

Eligible subjects were randomized in a 3:1 ratio to active (AR101; investigational biologic drug comprising peanut protein) or placebo in a one-day initial dose-escalation phase, where they received sequentially administered doses from 0.5 mg to 6 mg under supervision at the trial site. During the 20- to 40-week up dosing phase, subjects received a daily dose of peanut protein (AR101) or placebo. Doses were increased biweekly until a 300 mg dose was reached and maintained for 3 months (3 mg initial to 300 mg final). During the maintenance phase, subjects received a daily dose at home of 300 mg peanut protein for 12 weeks. An exit DBPCFC was performed at the end-of-trial visit with additional 600 mg and 1,000 mg peanut protein challenge doses, as tolerated. The primary endpoint was the proportion of participants who could consume a single dose of 1,000 mg peanut protein (~3-4 peanut kernels) without dose-limiting symptoms at exist DBPCFC. Additional endpoints included adverse event (AE) frequency and severity, and changes in food allergy-related quality of life (QoL).

QoL was assessed using the FAQLQ and FAIM measures. Age-appropriate versions of FAQLQ and FAIM were completed by participants aged 8-12 and 13-17 years of age, and all caregivers at two time points during the trial: before the screening DBPCFC and at the end-of-trial visit, immediately after the exit DBPCFC and unblinding. Both instruments utilized a seven-point scale where one indicates minimal impairment, seven indicates maximal impairment and a change of ≥0.5 is considered to have exceeded the developer-referenced minimal important difference (MID).

B) Results. All primary and secondary endpoints were met. 77 of the 132 (58.3%) actively treated participants tolerated a 1,000 mg peanut protein exit challenge dose compared with 1 (2.3%) on placebo (treatment difference: 56.0%; 95% CI: 44.1, 65.2; p<0.0001).

Significant improvements in self-reported and caregiver proxy-reported quality of life assessments were found in participants who received AR101. Improved QoL was self-reported in participants aged 8-12 in the active group across all FAQLQ domains. Improvements were statistically significant for the total score and for the "Allergen avoidance and dietary restrictions" and "Risk of accidental exposure" domains (LS mean difference active—placebo [95% CI]: −1.09 [−1.95, −0.22]; −1.18 [−2.06, −0.30]; −1.20 [−2.26, −0.15]; respectively; p<0.05 for all).

Figure 4:
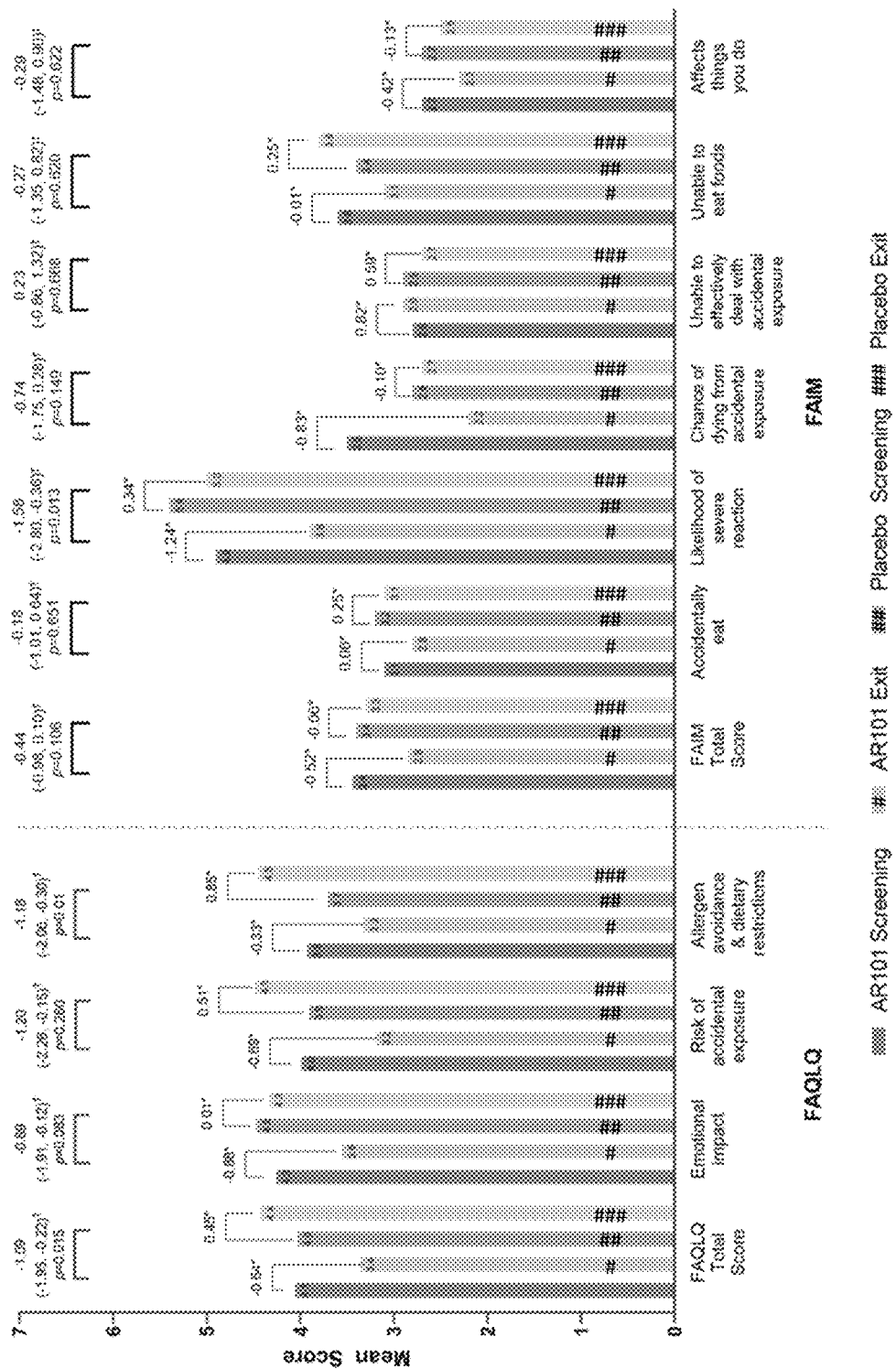
FIG. 4 shows FAQLQ and FAIM total scores and domain scores as reported by participants aged 8-12 years from a European clinical trial of AR101 at active group screening (first line of each total score or domain score), active group exit (second line of each total score or domain score), placebo group screening (third line of each total score or domain score), and placebo group exit (fourth line of each total score or domain score).
Figure 5:
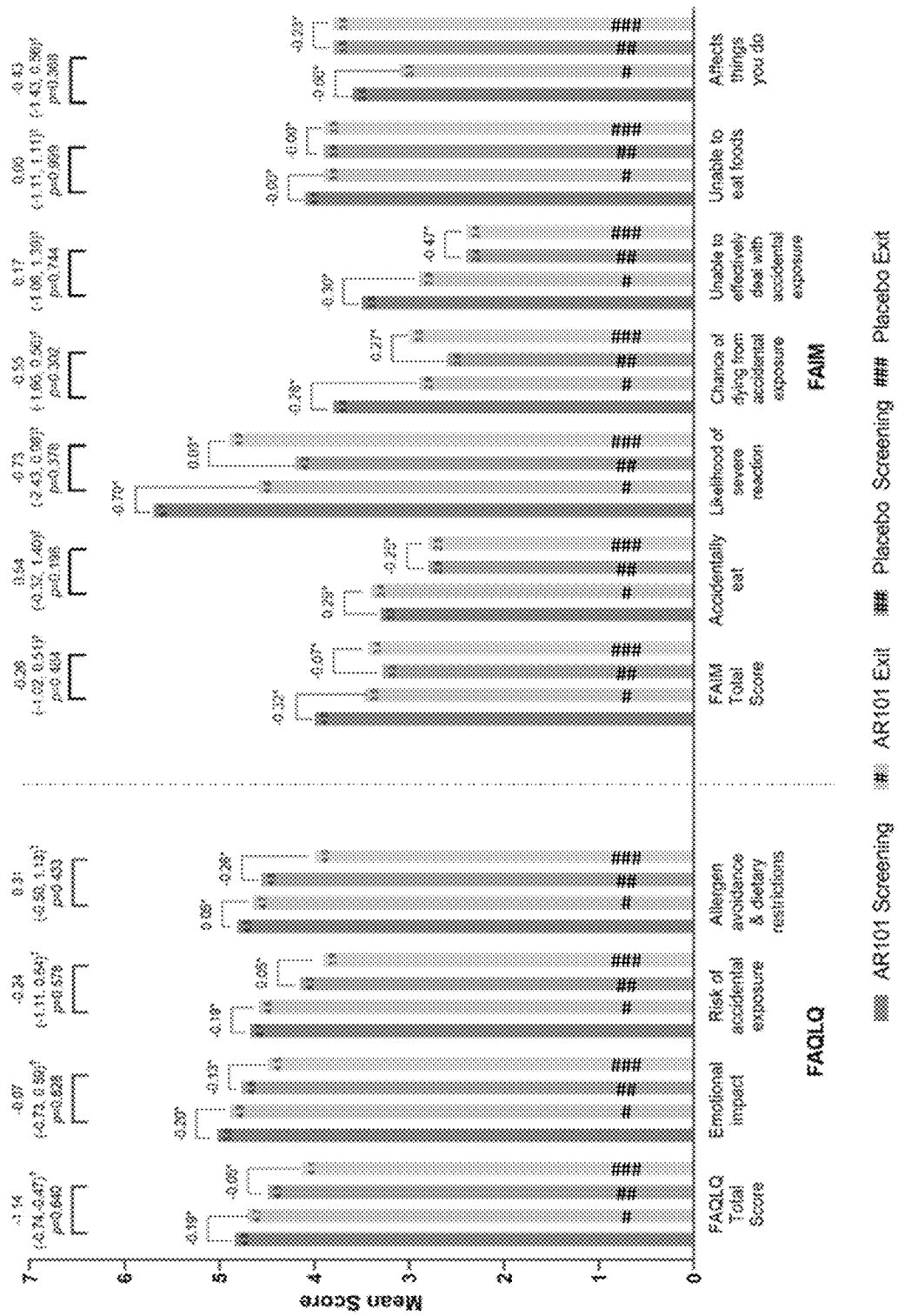
FIG. 5 shows FAQLQ and FAIM total scores and domain scores as reported by participants aged 13-17 years from a European clinical trial of AR101 at active group screening (first line of each total score or domain score), active group exit (second line of each total score or domain score), placebo group screening (third line of each total score or domain score), and placebo group exit (fourth line of each total score or domain score).
Figure 6:
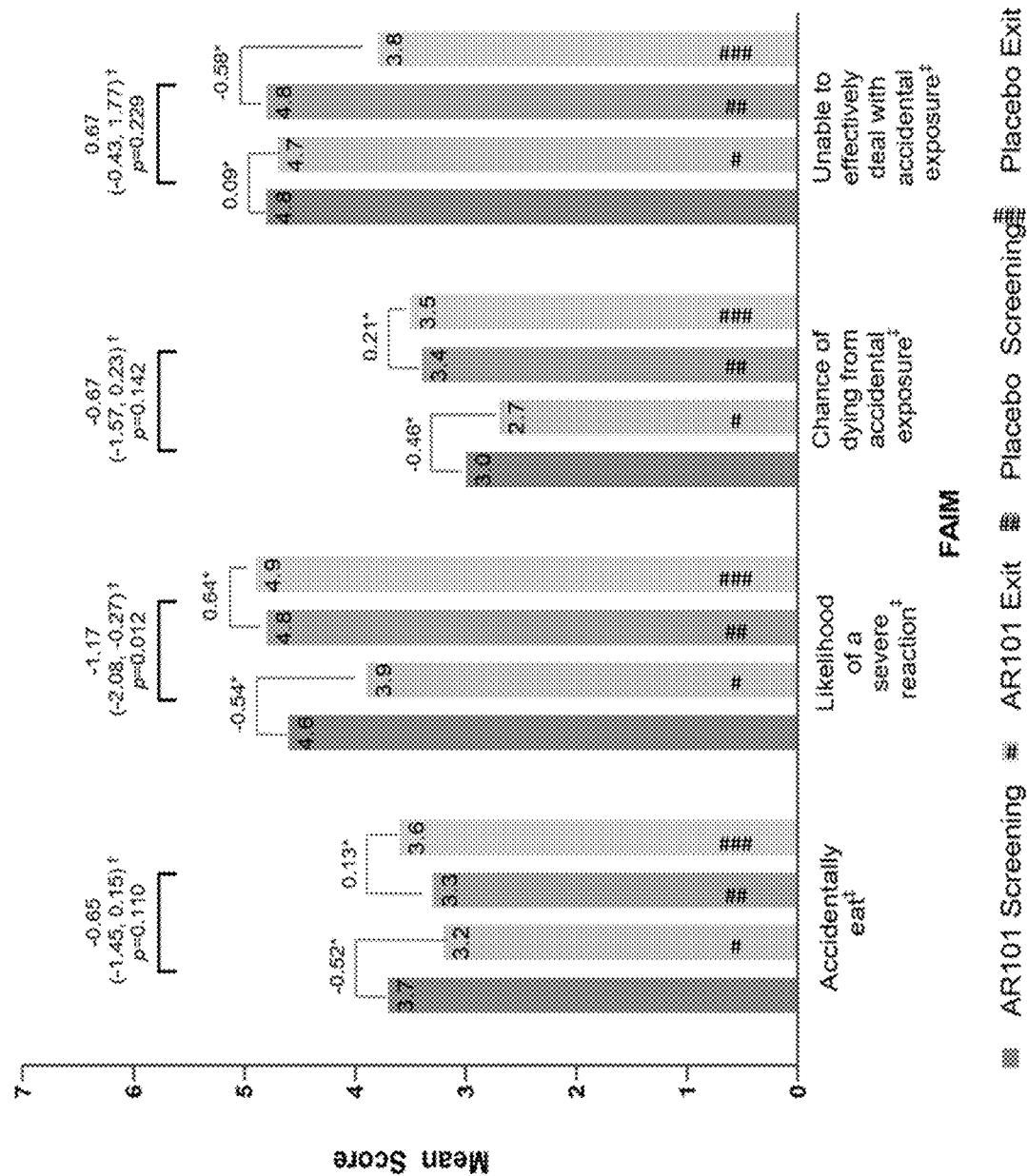
FIG. 6 shows proxy-reported FAIM scores across domains as reported by caregivers of participants aged 4-12 years from a European clinical trial of AR101 at active group screening (first line of each domain), active group exit (second line of each domain), placebo screening (third line of each domain), and placebo exit (fourth line of each domain).

Improvements in self-reported and proxy-reported QoL were observed to varying degrees across all FAIM domains. Compared to the placebo group, improved scores that exceeded MID for the domains "likelihood of a severe reaction" and "chance of dying from accidental allergen exposure" were self- and proxy-reported by participants and caregivers in the active group, respectively. Improved scores were proxy- and self-reported by caregivers for the domain "effectively treat/be treated upon accidental exposure" (LS mean treatment different active—placebo [95% CI] caregivers 4-12 years self-report: 0.85 [−0.17, 1.88] p>0.05; caregivers 4-12 years proxy-report: 0.67 [−0.43, 1.77] p>0.05; caregivers 13-17 years self-report: 0.98 [0.03, 1.94] p=0.04). The FAQLQ and FAIM results are summarized in FIGS. 4-6.

Due to exposure to allergenic material, active participants, as expected, experienced increased treatment-related adverse events compared with the placebo group, which might reduce quality of life. Against this expectation, no worsening of QoL that reached the MID was observed in any FAQLQ or FAIM domains in the active group compared with the placebo group.

What is claimed is:

1. A method of improving the quality of life of a patient with a peanut allergy, comprising:
administering to the patient a peanut composition according to an oral immunotherapy schedule comprising an up-dosing phase and a maintenance phase; wherein the peanut composition is administered to the patient during the maintenance phase of the oral immunotherapy schedule at a dose of about 300 mg peanut protein.

2. The method of claim 1, further comprising informing the patient that the peanut composition is being administered to the patient.

3. The method of claim 2, wherein the patient is informed that the peanut composition is being administered to the patient at the start of the oral immunotherapy schedule.

4. The method of claim 2, wherein the patient is informed that the peanut composition is being administered to the patient prior to the start of the oral immunotherapy schedule.

5. The method of claim 2, wherein the patient is informed that the peanut composition is being administered to the patient during the up-dosing phase of an oral immunotherapy schedule.

6. The method of claim 2, wherein the patient is informed that the peanut composition is being administered to the patient during the maintenance phase of the oral immunotherapy schedule.

7. The method of claim 2, wherein the method comprises measuring the quality of life after informing the patient that the peanut composition is being administered.

8. The method of claim 1, wherein the quality of life improvement is measured using a quality of life questionnaire (QoLQ).

9. The method of claim 8, wherein the QoLQ comprises one or more scored domains of measurement.

10. The method of claim 9, wherein the QoLQ is a Food Allergy Quality of Life Questionnaire (FAQLQ).

11. The method of claim 10, wherein the FAQLQ is a FAQLQ-child form (FAQLQ-CF), FAQLQ-teen form (FAQLQ-TF), FAQLQ-adult form (FAQLQ-AF), or FAQLQ-parent form (FAQLQ-PF).

12. The method of claim 9, wherein the one or more scored domains of the QoLQ are each scored on a scale between 1 and 7, or are each converted to a score between a first score and a second score, wherein the second score indicates worse quality of life.

13. The method of claim 9, wherein an improvement in the patient's quality of life is at least 0.5 points in one or more domains of the QoLQ at a second time point after a period of oral immunotherapy as compared to an assessment at a first time point before the period of oral immunotherapy.

14. The method of claim 13, wherein the period of oral immunotherapy between the first time point and the second time point is the up-dosing phase of the oral immunotherapy schedule.

15. The method of claim 13, wherein the period of oral immunotherapy between the first time point and the second time point is at least 1 month of a maintenance therapy of the oral immunotherapy schedule.

16. The method of claim 9, wherein an improvement in the patient's quality of life is at least 0.5 points in a total score of the QoLQ at a second time point after a period of oral immunotherapy as compared to an assessment at a first time point before the period of oral immunotherapy; wherein the total score is the average of each domain score.

17. The method of claim 8, wherein the QoLQ is a Food Allergy Independent Measure (FAIM).

18. The method of claim 17, wherein the FAIM is a FAIM-child form (FAIM-CF), FAIM-teen form (FAIM-TF), FAIM-adult form (FAIM-AF), or FAIM-parent form (FAIM-PF).

19. The method of claim 1, wherein the quality of life is improved for at least 6 months.

20. The method of claim 1, wherein the quality of life is improved for at least 12 months.

21. The method of claim 1, wherein the quality of life improves after 6 months of the oral immunotherapy schedule.

22. The method of claim 1, wherein the peanut composition is administered to the patient during the maintenance phase on a daily basis.

23. The method of claim 1, wherein the maintenance phase is at least 3 months.

24. The method of claim 1, wherein the up-dosing phase comprises administering to the patient two or more different doses between about 3 mg and about the dose of an initial maintenance phase dose.

25. The method of claim 1, wherein the up dosing phase is between about 3 months and about 2 years in length.

26. The method of claim 1, wherein the oral immunotherapy schedule further comprises an initial escalation phase.

27. The method of claim 1, wherein the patient is about 4 years old or older.

28. The method of claim 1, wherein the patient is between about 4 years old and about 17 years old.

29. The method of claim 1, wherein the patient is between about 8 years old and about 17 years old.

30. The method of claim 1, wherein the method comprises measuring the quality of life before administering to the patient a peanut composition according to an oral immunotherapy schedule.

31. The method of claim 1, wherein the method comprises measuring the quality of life after administering to the patient a peanut composition according to an oral immunotherapy schedule.

32. The method of claim 1, wherein the quality of life of the patient is improved as determined by a quality of life questionnaire (QoLQ).

33. A method of improving the quality of life of a patient with a peanut allergy, as assessed by a quality of life questionnaire (QoLQ), the method comprising administering to the patient a peanut composition according to an oral immunotherapy schedule comprising an up-dosing phase and a maintenance phase; wherein the peanut composition is administered to the patient during the maintenance phase of the oral immunotherapy schedule at a dose of about 300 mg peanut protein.

* * * * *